(12) United States Patent
Yeatman et al.

(10) Patent No.: US 9,037,416 B2
(45) Date of Patent: May 19, 2015

(54) GENOTYPIC TUMOR PROGRESSION CLASSIFIER AND PREDICTOR

(75) Inventors: Timothy Yeatman, Thonotosassa, FL (US); Steven Alan Enkemann, Lutz, FL (US); Steven Eschrich, Lakeland, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 985 days.

(21) Appl. No.: 12/728,840

(22) Filed: Mar. 22, 2010

(65) Prior Publication Data

US 2010/0240540 A1 Sep. 23, 2010

Related U.S. Application Data

(63) Continuation of application No. PCT/US2008/077190, filed on Sep. 22, 2008.

(60) Provisional application No. 60/974,264, filed on Sep. 21, 2007.

(51) Int. Cl.
*G01N 33/50* (2006.01)
*C12Q 1/68* (2006.01)

(52) U.S. Cl.
CPC ........ *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,530,412 | A | 6/1996 | Goldblum |
| 2003/0008620 | A1 | 1/2003 | Rowell et al. |
| 2005/0085223 | A1 | 4/2005 | Liu |
| 2005/0176376 | A1 | 8/2005 | Liu |
| 2006/0094021 | A1 | 5/2006 | Costa et al. |
| 2006/0141504 | A1 | 6/2006 | Willman et al. |
| 2006/0195269 | A1 * | 8/2006 | Yeatman et al. ............. 702/20 |
| 2006/0233111 | A1 | 10/2006 | Wright |
| 2007/0196041 | A1 | 8/2007 | Mitchell, Jr. et al. |
| 2009/0011439 | A1 * | 1/2009 | Weichselbaum et al. .... 435/7.23 |

OTHER PUBLICATIONS

Wahde et al. (Improving the prediction of the clinical outcome of breast cancer using evolutionary algorithms, Soft. Comput, 2006, vol. 10, pp. 338-345).*
Mithat et al. (Concordance probability and discriminatory power in proportional hazards regression, 2005, pp. 965-970).*
Van Gelder et al., Amplified RNA Synthesized from Limited Quantities of Heterogeneous cDNA, Proc. Natl. Acad. Sci. USA, 1990, vol. 87, pp. 1663-1667.
Dobbin et al., Interlaboratory Comparability Study of Cancer Gene Expression Analysis Using Oligonucleotide Microarrays, Clinical Cancer Research, 2005, vol. 11, pp. 565-572.
Gonen et al., Concordance Probability and Discriminatory Power in Proportional Hazards Regression, Biometrika, 2005, vol. 92, No. 4, pp. 965-970.
Booth et al., Adjuvant Chemotherapy for Resected Non-Small Cell Lung Cancer, Journal of Thoracic Oncology, 2006, vol. 1, No. 2., pp. 180-187.
Gandara et al., Adjuvant Chemotherapy of Stage 1 Non-Small Cell Lung Cancer in North America, Journal of Thoracic Oncology, 2007, vol. 2, No. 7, pp. S125-S127.
Jemal et al., Cancer Statistics, 2006, A Cancer Journal for Clinicians, 2006, vol. 56, pp. 106-130.
Li et al., Model-Based Analysis of Oligonucleotide Arrays: Expression Index Computation and Outlier Detection, PNAS, 2001, vol. 98, No. 1, pp. 31-36.
Shepherd et al., Erlotinib in Previously Treated Non-Small-Cell Lung Cancer, The New England Journal of Medicine, 2005, vol. 353, No. 2, pp. 123-132.
Shedden et al., Gene Expression-Based Survival Prediction in Lung Adenocarcinoma: A Multi-Site, Blinded Validation Study: Director's Challenge Consortium for the Molecular Classification of Lung Adenocarcinoma, Nature Medicine, 2008, vol. 14, No. 8, pp. 822-827.
International Search Report for PCT/US08/77190 dated Sep. 22, 2008.
Chen et al., Protein Profiles Associated with Survival in Lung Adenocarcinoma, PNAS, 2003, vol. 100, No. 23, pp. 13537-13542.
Chen et al., A Five-Gene Signature and Clinical Outcome in Non-Small-Cell Lung Cancer, The New England Journal of Medicine, 2007, vol. 356, No. 1, pp. 11-20.
Potti et al., A Genomic Strategy to Refine Prognosis in Early-Stage Non-Small-Cell Lung Cancer, The New England Journal of Medicine, 2006, vol. 355, No. 6, pp. 570-580.
Powell et al., Gene Expression in Lung Adenocarcinomas of Smokers and Nonsmokers, Am. J. Respir. Cell Mol. Biol., 2003, vol. 29, pp. 157-162.
Miura et al., Laser Capture Microdissection and Microarray Expression Analysis of Lung Adenocarcinoma Reveals Tobacco Smoking- and Prognosis-Related Molecular Profiles, 2002, Cancer Research, vol. 62, pp. 3244-3250.

(Continued)

*Primary Examiner* — Jason Sims
(74) *Attorney, Agent, or Firm* — Robert J. Varkonyi; Smith & Hopen, P.A.

(57) ABSTRACT

Actively dividing tumors appear to progress to a life threatening condition more rapidly than slowly dividing tumors. Assessing actively dividing tumors currently involves a manual assessment of the number of mitotic cells in a histological slide prepared from the tumor and assessed by a trained pathologist. Disclosed is a method for using cumulative information from a series of expressed genes to determine tumor prognosis. This cumulative information can be used to categorize tumor samples into high mitotic states or low mitotic states using a mathematical algorithm and gene expression data derived from microarrays or quantitative-Polymerase Chain Reaction (Q-PCR) data. The specific mathematical description outlines how the algorithm assesses the most informative subset of genes from the full list of genes during the assessment of each sample.

9 Claims, 9 Drawing Sheets

(56) References Cited

OTHER PUBLICATIONS

Sultan et al., Binary Tree-Structured Vector Quantization Approach to Clustering and Visualizing Microarray Data, Bioinformatics, 2002, vol. 18, Suppl. 1, pp. S111-S119.

Tusher et al., Significance Analysis of Microarrays Applied to the Ionizing Radiation Response, PNAS, 2001, vol. 98, No. 9, pp. 5116-5121.

Beer et al., Gene-Expression Profiles Predict Survival of Patients with Lung Adenocarcinoma, Nature Medicine, 2002, vol. 8, No. 8, pp. 816-824.

Hsieh et al., Sample-Size Calculations for the Cox Proportional Hazards Regression Model with Nonbinary Covariates, Controlled Clinical Trials, 2000, vol. 21, pp. 552-560.

Wikipedia, Proportional Hazard Models. Accessed on Aug. 29, 2012. http://en.wikipedia.org/wiki/propertional_hazards-models.

\* cited by examiner

|  | UM | HLM | CAN/DF | MSK |
|---|---|---|---|---|
| Sample size | 177 | 79 | 82 | 104 |
| Age (mean, s.d.) | 64(10) | 67(10) | 61(10) | 65(10) |
| Sex (% male) | 56% | 51% | 55% | 36% |
| Stage I | 66% | 54% | 68% | 61% |
| Stage II | 16% | 26% | 32% | 19% |
| Stage III | 18% | 19% | 0% | 20% |
| Median follow up (months) | 54 | 39 | 40 | 43 |
| Number of deaths | 75 | 50 | 28 | 34 |

| Classifier Conditions | Hazard ratio | 95% CI | p-value | CPE |
|---|---|---|---|---|
| MSK test set, all stages | 2.71 | (1.36, 5.42) | 0.004 | 0.634 |
| CAN/DF test set, all stages | 2.14 | 1.08, 4.23 | 0.025 | 0.621 |
| MSK test set, stage 1 only | 2.92 | (0.94, 9.10) | 0.060 | 0.640 |
| CAN/DF test set, stage 1 only | 2.33 | (0.90, 6.08) | 0.077 | 0.638 |

|  | All stages | | | | Stage 1 only | | | |
| --- | --- | --- | --- | --- | --- | --- | --- | --- |
|  | MSK | | CAN/DF | | MSK | | CAN/DF | |
|  | Sens | Spec | Sens | Spec | Sens | Spec | Sens | Spec |
| >=0 | 1.00 | 0.00 | 1.00 | 0.00 | 1.00 | 0.00 | 1.00 | 0.00 |
| >=1 | 0.81 | 0.56 | 0.74 | 0.44 | 0.98 | 0.65 | 0.61 | 0.50 |
| >=2 | 0.08 | 0.88 | 0.18 | 0.78 | 0.24 | 0.93 | 0.11 | 0.81 |
| >2 | 0.00 | 1.00 | 0.00 | 1.00 | 0.00 | 1.00 | 0.00 | 1.00 |

GENOTYPIC TUMOR PROGRESSION CLASSIFIER AND PREDICTOR

CROSS REFERENCE TO RELATED APPLICATIONS

This application is a continuation of prior filed International Application, Serial Number PCT/US2008/077190 filed Sep. 22, 2008, which claims priority to U.S. provisional patent application No. 60/974,264 filed Sep. 21, 2007 which is hereby incorporated by reference into this disclosure.

STATEMENT OF GOVERNMENT INTEREST

This invention was made with Government support under Grant No. DAMD 17-02-2-0051 awarded by the Department of Defense and Grant No. CA085052 awarded by the National Institutes of Health. The Government has certain rights in the invention.

FIELD OF INVENTION

This invention relates to oncogenic assessment using cumulative information obtained from expression of genes involved in regulation of cell cycle and mitosis.

BACKGROUND OF THE INVENTION

In the United States and in many Western countries, lung cancer represents the leading cause of cancer-related death (Jemal, A. et al. Cancer Statistics 2006. CA Cancer J. Clin. 56, 106-130 (2006). The National Cancer Institute of the U.S. National Institutes of Health estimated there were 215,020 new cases of lung cancer and 161,840 lung cancer-related deaths within the U.S. in 2008. Lung cells cancers are classified into two main types, small cell lung cancer (SCLC) and non small cell lung cancer (NSCLC).

Cell classification and typing is typically performed using light microscopy, immunohistochemistry, physical examination, chest x-ray, and chest computed tomography (CT) scan with infusion of contrast material. Diagnosis generally requires review of pathologic material by an experienced lung cancer pathologist to manually assess the number of mitotic cells in a histological slide prepared from the tumor. Tumor classification is vitally important because small cell lung cancer, which responds well to chemotherapy and is generally not treated surgically, can be confused on microscopic examination with non-small cell carcinoma, for which treatment normally consisting of surgical resection. Additionally, staging procedures are important to distinguish localization and tumor aggressiveness. Determining cancer stage non-surgically provides better assessment of prognosis, and aides in treatment determination, which is usually influenced by stage, particularly when chest radiation therapy or surgical excision is added to chemotherapy for patients with limited-stage disease.

SCLCs are the most aggressive pulmonary tumor, with median survival from diagnosis of 2 to 4 months. Localized (limited) SCLC tumors are confined to the hemithorax of origin, the mediastinum, or the supraclavicular lymph nodes, and treatment includes surgical rescission, with or without chemotherapy. Extensive-stage disease, where tumor has spread beyond the supraclavicular area, possess worse prognosis than limited-stage tumors.

NSCLCs are a heterogeneous aggregate of tumors, with the most common histologies epidermoid or squamous carcinoma, adenocarcinoma, and large cell carcinoma. These histologies are often classified together because approaches to diagnosis, staging, prognosis, and treatment are similar. The first classification of tumors are surgically resectable (generally stage I, stage II, and selected stage III tumors), and possess the best prognosis, which depends on a variety of tumor and host factors. In some cases, tumors are alternatively treated with curative radiation therapy or chemotherapy. The second group of tumors is locally (T3-T4) and/or regionally (N2-N3) advanced lung cancer, which are treated with combination therapies, such as radiation therapy in combination with chemotherapy or surgical resection and either preoperative or postoperative chemotherapy or chemoradiation therapy. The final tumor group is metastatic tumor with distant metastasis (M1) at the time of diagnosis. Current treatment is radiation therapy or chemotherapy for palliation.

The 5-year, overall survival rate of 15% has not improved over many decades, mainly because approximately two-thirds of lung cancers are discovered in advanced stages, for which cure by surgical resection is no longer an option. Furthermore, even among early-stage patients who are treated to primarily by surgery with curative intent, 30-55% will develop and die of metastatic recurrence. Recent multinational clinical trials (IALT, JBR10, ANITA, UFT, LACE) conducted in several continents have demonstrated that adjuvant chemotherapy significantly improves the survival of patients with early-stage (IB-II) disease (Booth, C. M. & Shapard F. A. Adjuvant chemotherapy for resected non-small cell lung cancer. J. Thorac. Oncol. 2, 180-187 (2006)). Nevertheless, it is clear that a proportion of patients with stage I disease have poorer prognosis and may benefit significantly from adjuvant chemotherapy, whereas some with stage II disease with relatively good prognoses may not benefit significantly from adjuvant chemotherapies. It remains possible, however, that the latter patients could derive additional benefit from adjuvant targeted therapies (Booth, C. M. & Shepherd, F. A. Adjuvant chemotherapy for resected non-small cell lung cancer. J. Thorac. Oncol. 2, 180-187 (2006); Gandara, D. R., et al., Adjuvant chemotherapy of stage I non-small cell lung cancer in North America. J. Thorac. Oncol. 7(suppl. 3), S125-S127 (2007); Shepherd, F. A., et al. Erlotinib in previously treated non-small-cell lung cancer. N. Engl. J. Med. 353, 123-132 (2005)).

Therefore, there is an urgent need to establish new diagnostic paradigms and validate in clinical trials methods for improving the selection of stage I-II patients who are most likely to benefit from adjuvant chemotherapy.

SUMMARY OF THE INVENTION

Disclosed is a method of predicting clinical tumor outcome by providing gene expression from a tumor sample (Shedden, K., et al., ene expression-based survival prediction in lung adenocarcinoma: a multi-site, blinded validation study. Nat. Med. 14(8):822-7. (2008)). The gene expression may be obtained from any number of means known in the art, including without limitation, PCR, Chip, gene array, microarrays or quantitative-Polymerase Chain Reaction (Q-PCR), and reverse transcriptase Polymerase Chain Reaction (rt-PCR). At least one threshold value is defined for classifying the gene expression levels. In certain embodiments, two threshold values are used. A vote of single-gene classifiers is then determined by comparing the gene expressions to the threshold value or values, followed by selecting genes with expression levels above at least one threshold value and selecting genes with expression levels below at least one threshold value. This data is then used to calculate the majority vote classifier.

In certain embodiments, at least one threshold value consists of an upper threshold value and lower threshold value. These values are the upper 33% of the gene expression values, the lower 33% of the gene expression values; or the upper 15% of the gene expression values, and the lower 15% of the gene expression values in specific embodiments. In alternative embodiments, hazard ratios are determined for the risk score, wherein a hazard ratio is calculated from the majority vote classifier and a score greater than 1 indicates poor clinical outcome.

Certain embodiments of the invention also assign numerical values to the gene expression; +1 to gene expression values at and above the upper threshold value, −1 to gene expression values at and below the lower threshold value, and 0 to gene expression values above the lower threshold value and below the upper threshold value. In specific embodiments, these values are added together to calculate the majority vote classifier. By further defining at least one majority vote threshold value, the majority vote classifier is compared to at least one majority vote threshold value.

Alternatively, only one threshold value is used, with numerical values used for the gene expression; +1 to gene expression values at and above the threshold value and −1 to gene expression values at and below the threshold value. In specific embodiments, these values are added together to calculate the majority vote classifier. By further defining at least one majority vote threshold value, the majority vote classifier is compared to at least one majority vote threshold value, determining tumor outcome.

In some embodiments, the method uses a probeset list generated by providing a first probeset list, and testing the first probeset list against other gene expression data for a tumor cell. This gene expression data is compared to two threshold values, and probes identified as significantly related to the first probeset list's gene expression, either as through high expression or through low expression, are used in a second probeset list test. A second probeset list, including probes selected in the first test, are compared to gene expression data for a tumor cell using the two threshold values, as before. Probes identified as significantly related to gene expression in the second probeset list are included in a third probeset list test. This third probeset list is tested against gene expression data for a tumor cell, as before. Probes selected from the third probeset are then included in the probelist.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Disclosed is a tumor prognosis predictor based on gene expression signatures of lung adenocarcinomas. Gene expression data is used to identify patients with slightly more aggressive forms of cancer, like adenocarcinoma, that might require closer monitoring or chemotherapeutic intervention. The invention uses cumulative expression information from a series of genes involved in the regulation of the cell cycle and the mitotic process to assess the overall mitotic state of a tumor sample. This cumulative information can be used to categorize tumor samples into high mitotic states or low mitotic states using a mathematical algorithm and gene expression data derived from microarrays or quantitative-Polymerase Chain Reaction (Q-PCR) data. The specific mathematical description outlines how the algorithm assesses the most informative subset of genes from the full list of genes during the assessment of each sample A mechanistic classifier was produced using training data and tested for effectiveness using two different data sets. To ensure scientific validity of the results, subject samples along with all relevant clinical, pathological and outcome data were collected by investigators at four institutions using data from six lung-cancer treatment sites with subject inclusion criteria defined a priori. Gene expression data on subsets of lung adenocarcinomas were generated by each of four different laboratories using a common platform and following a protocol previously demonstrated to be robust and reproducible (Dobbin, K. K. et al. Interlaboratory comparability study of cancer gene expression analysis using oligonucleotide microarrays. Clin. Cancer Res. 11, 565-572 (2005)).

Figures 1, 2, 3:
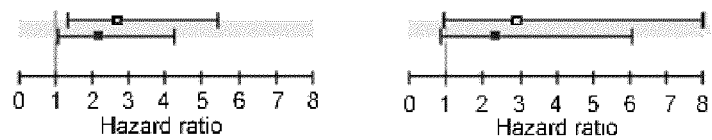
FIG. 1 is a table of the data set characteristics for the tumor samples.
FIG. 2 is a graph of the classifier performance. Hazard ratios are displayed for the validation set along with 95% confidence intervals.
FIG. 3 is a table depicting hazard ratios and confidence data values for the classifier.
Figure 4:
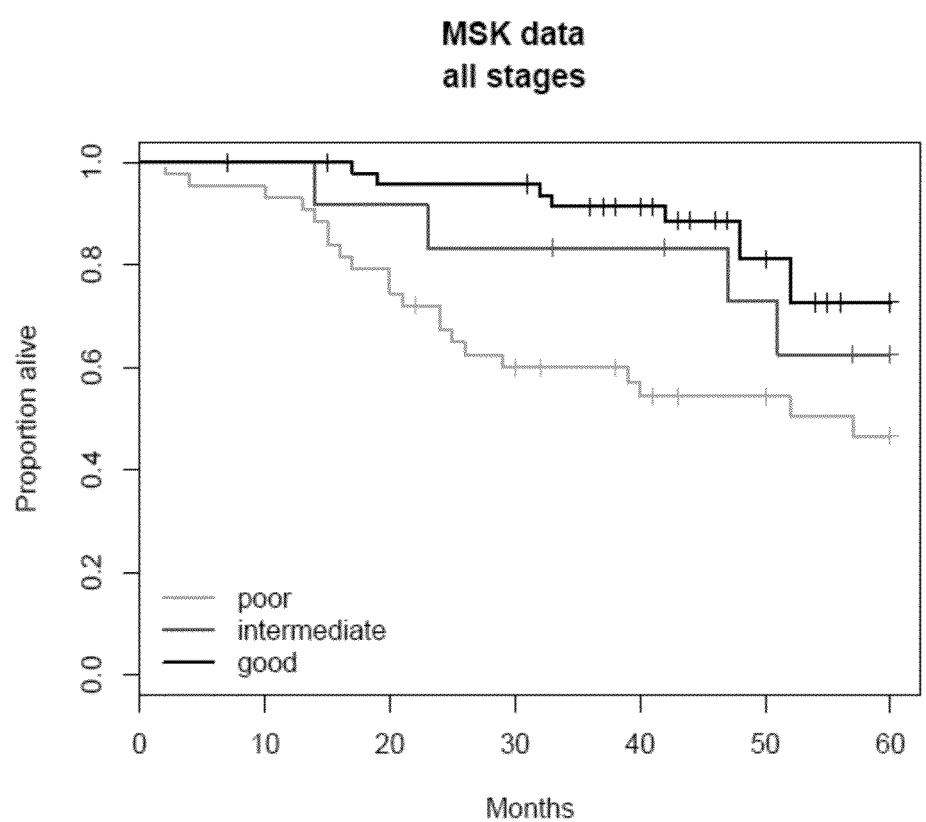
FIG. 4 is a graph of Kaplan-Meier estimates of survivor function for the MSK validation set using all tumor stages. Low scores correspond to the lowest predicted risk and high scores correspond to the greatest predicted risk.
Figure 5:
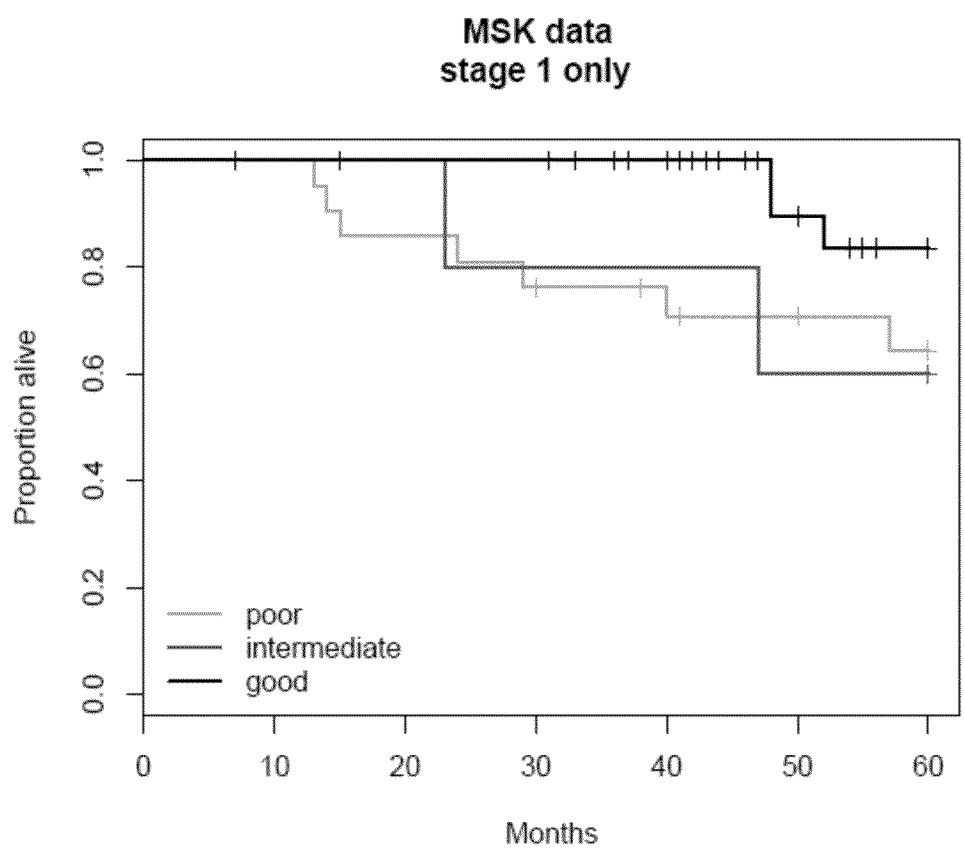
FIG. 5 is a graph of Kaplan-Meier estimates of survivor function for the MSK validation set using only stage I tumors. Low scores correspond to the lowest predicted risk and high scores correspond to the greatest predicted risk.
Figure 6:
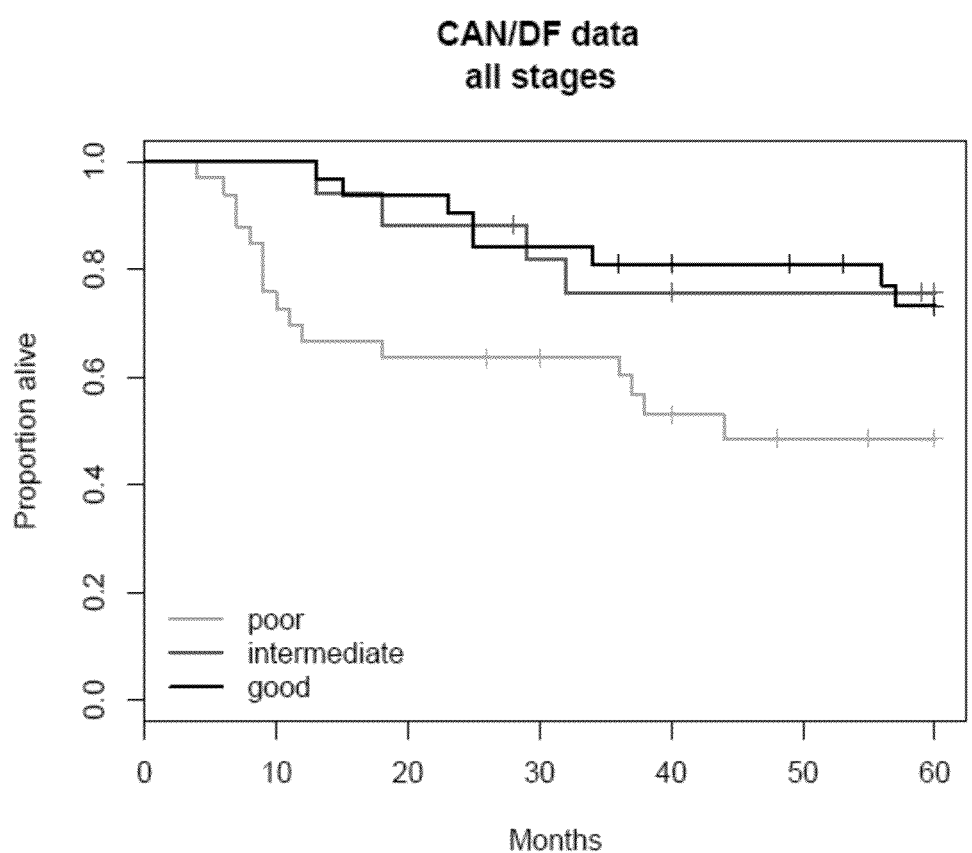
FIG. 6 is a graph of Kaplan-Meier estimates of survivor function for the CAN/DF validation set using all tumor stages. Low scores correspond to the lowest predicted risk and high scores correspond to the greatest predicted risk.

Four different data sets were generated, as described in FIG. 1, designated as HLM, UM, MSK and CAN/DF. Data generated at the HLM site was used as a training set and the results were validated using the independent data sets from the other three sites following a blinded protocol. Initial evaluation of the gene expression data suggested that the data from the UM, HLM and MSK were broadly similar, although distinguishable, but the data from CAN/DF showed some systematic differences from the other three sites due mainly to reduced signal intensity.

Approximately 505 adenocarcinoma samples varying from stage I to stage III were collected, with about 60% of the samples represented by stage I tumors. The tumors were collected by surgical resection from patients prior to chemotherapy or radiation. Two years of follow-up information was available for each tumor sample. Study pathologists reviewed the tumor permanent sections and frozen sections of the samples to identify stage, diagnosis, and regions of the frozen section containing the maximum tumor cellularity for macrodissection. Regions containing a minimum of 60% tumor cellularity were required, and in most instances tumor cellularity of at least 70-90% was identified for inclusion in the sample for RNA isolation. A second pathological review of each case was performed to coordinate the pathological information across all tumor collection sites to verify the initial pathological findings. Where the pathological diagnosis and review disagreed, the samples were excluded from the study. Clinical information was also collected for tumor staging, history of prior cancers, lymph node involvement by lymph node dissection/sampling, smoking history, age, gender, operation type, last follow-up date, and patient's status. Additional information useful to the study, including CXR and CT scans, pulmonary function tests, time and site of recurrence, and adjuvant treatment information was collected where available. Survival outcome was determined and most patients have reliable long-term follow-up. Patients were censored after 60 months of follow-up or excluded for analysis where death occurred within 1 month of operation.

The clinical data collected from each individual site underwent two forms of review. A core set of critical covariates were identified for thorough quality assessment, and reviewed by an NCI statistician to evaluate discrepancies in coding patterns between sites, logical inconsistencies in the data, and missing data. The complete dataset underwent a second round of quality review by the CALGB Statistical Center Data Operations prior to finalizing the clinical dataset.

Multiple comparison adjustment in the context of predictor development involves a tradeoff. Very strict Bonferroni-type adjustment may reduce predictor performance by eliminating informative genes. Too lax adjustment may reduce predictor performance by inclusion of too many noise genes. It was thought that the significance level used in the sample size calculation represented a reasonable tradeoff between the two. A total of 486 tumor samples were arrayed and a total of 442 samples were retained after the QC evaluation of the clinical, pathological, and array data.

Frozen dissected tumor tissue was immersed in 1 ml of Trizol Reagent (Invitrogen Corp., Carlsbad, Calif.). Tissue sections were disrupted with a glass homogenizer or glass beads to facilitate dissolution in the Trizol reagent as necessary. Purification of the RNA from the Trizol dissolved samples followed the manufacturer's cleanup procedure (Qiagen Inc., Valencia, Calif.). The quality of total RNA was assessed by electrophoretic analysis on a bioanalyzer (Agilent 2100). RNA yields were determined by $OD_{260}$ measurements.

RNA extracts were then labeled for hybridization. The poly(A) RNA pool of total RNA extracts were converted to cDNA and amplified and labeled with biotin following the procedure initially described previously (Van Gelder, R. N., et al., Amplified RNA synthesized from limited quantities of heterogeneous cDNA. *Proc. Nat. Acad. Sci., U.S.A.,* 1990, 87(5):1663-7). First-strand cDNA synthesis was carried out using the Superscript Choice System (Invitrogen Corporation, Carlsbad, Calif.) and the T7 promoter/oligo (dT) primer (5'-GGCCAGTGAATTGTAATACGACTCAC-TATAGGGAGGCGG-(dT)$_{24}$-3'), (SEQ ID 1) from the T7-Oligo(dT) Promoter Primer Kit (Affymetrix Corporation, Santa Clara, Calif.). Following annealing, cDNA synthesis reaction solutions were added to establish final reaction conditions of 5 mg RNA, 100 μmol T7-(T)$_{24}$ primer, 500 mM each dNTP, 10 mM DTT, 50 mM Tris-HCl, pH 8.3, 75 mM KCl, 3 mM MgCl$_2$, and 200 U of Superscript II reverse transcriptase (Invitrogen). The reaction was incubated for 1 hr at 42° C., followed by a second-strand cDNA synthesis at 16° C. for 2 hr in a total volume of 150 mL, using 10 U of *E. coli* DNA ligase, 40 U of *E. coli* DNA polymerase I, and 2 U of *E. coli* RNase H in the presence of 200 mM of each dNTP, 10 mM NH$_4$SO$_4$, 1.3 mM DTT, 26.7 mM Tris-HCl, pH 7.0, 100 mM KCl, 5 mM MgCl$_2$, and 150 mM b-NAD$^+$ (Invitrogen Corp.). Following the second-strand DNA synthesis, 10 U of T4 DNA Polymerase (Invitrogen, Corp.) was added and the samples were incubated an additional 5 min at 16° C. The reaction was stopped by the addition of 0.5 M EDTA and the nucleic acids were purified using the Affymetrix GeneChip sample clean-up modules (#900371, Affymetrix). The nucleic acids were eluted with 25 ml of DEPC treated water. Twenty-two microliters of the purified cDNA was used as the template for a transcription reaction performed with the Bio-Array™ HighYield™ RNA Transcript Labeling Kit according to manufacturer's instructions (ENZO Life Sciences, New York, N.Y.) which incorporates biotinylated UTP into the transcripts. The Biotin-labeled RNA was purified using RNeasy columns (Qiagen Inc., Valencia, Calif.) and fragmented to a size of 35 to 200 bases by incubating at 940 C for 35 minutes in fragmentation buffer (40 mM Tris-acetate, pH 8.1/100 mM potassium acetate/30 mM magnesium acetate). The integrity of the starting material and the products of each reaction were monitored on agarose gels to assess the size distribution of the products and compare them to the starting material.

Array hybridization solutions (20 μg of fragmented RNA and 0.1 mg/ml sonicated herring sperm DNA, in 1×MES buffer (containing 100 mM MES, 1 M Na$^+$, 20 mM EDTA, and 0.01% Tween 20)) were made. Hybridization standards were made by spiking aliquots with known concentrations of RNA from the bacterial genes, BioB, BioC, and BioD, and one phage gene, Cre. The hybridization mixtures was heated to 99° C. for 5 min followed by incubation at 45° C. for 5 min before injection of the sample into an Affymetrix GeneChip array cartridge 133A. All hybridizations were carried out at 45° C. for 16-17 h with mixing on a rotisserie at 60 rpm. Following hybridization, the solutions were removed and the arrays were rinsed with 1×MES. The arrays were washed and stained using the GeneChip Fluidics station protocol EukGE_WS2, which consists of 10 cycles of 2 mixes per cycle with non-stringent wash buffer (6×SSPE, 0.01% Tween 20) at 25° C. followed by 4 cycles of 15 mixes per cycle with stringent wash buffer (100 mM MES, 0.1 M Na$^+$, and 0.01% Tween 20) at 50° C. The probe arrays were stained for 10 min in streptavidin-phycoerythrin solution (SAPE) [1×MES solution, 10 μg/ml SAPE (Molecular Probes, Eugene, Oreg.), and 2 μg/μl acetylated BSA (Invitrogen)] at 25° C., then washed for 10 cycles of 4 mixes per cycle at 25° C. The probe arrays were treated for 10 min with an antibody solution [1×MES solution, 2 μg/μl acetylated BSA, 0.1 μg/μl normal goat IgG (Sigma Chemical, St. Louis, Mo.), 3 μg/μl biotinylated goat-anti-streptavidin antibody, (Vector Laboratories, Burlingame, Calif.)] at 25° C. followed by a second staining for 10 min in SAPE at 25° C. The final wash was 15 cycles of 4 mixes per cycle at 30° C. with non-stringent wash buffer. The probe arrays were then scanned once at 1.56 μm resolution using the Affymetrix GeneChip Scanner 3000 or at 3 μm resolution using the Affymetrix GeneChip Scanner 2500.

Arrays were visually scanned for any defects or scanning artifacts that might compromise the final results. Data was then transferred to an honest broker system for further work. From a combined analysis by two independent testing facilities, a small number of arrays were excluded under the suspicion of poor quality array data. The HLM dataset for all tumor stages and for stage 1 were used as the training set, with the data from UM and MSK held out as an external validation datasets containing similar microarray data and the data from the DF site held out as a more challenging external test set. The datasets sites were quantile normalized as a group using the array NCl_U133A__61L as a reference file and imported into the software dChip (Li et al, 2001) (Build version February 2006) and signal values for each probeset were calculated using the default settings. The calculated microarray data was then combined with the clinical data for each sample and assigned a sample number by the honest broker.

The data for the validation sets CAN/DF and MSK were held by a third-party 'honest broker' during analysis of the training data. Risk scoring procedures were developed on the training data and a prognostic model developed on the training data. After the model was defined and documented, the honest broker released the gene expression and clinical data (but not the outcome data) for the two validation data sets, which was tested on the prognostic model to predict outcomes for each subject. These predicted risk scores were then passed back to the honest broker, allowing evaluation of the performance of the prognostic models.

Overall, 44 of the 486 arrayed samples (including one Stratagene reference sample) were excluded from the study based on violations of the clinical criteria that were discovered after the initial sample was defined, or due to poor array quality. Eleven of the patient samples, and the single excluded Stratagene sample, were excluded due to quality-control problems with the microarray data, with the remaining 33 samples excluded due to violations of clinical and pathological criteria.

The probesets and thresholds for classification were selected using an iterative application of the classification process. An initial list of 614 probesets were developed using data collected from public databases and original data. Cell line data from fast growing cells, versus slow growing cells, was used to correlate expression of replication factor C and MCM7. This served as the initial gene set $G_1$, which are believed to function in cell division or otherwise aid in progressing through the cell cycle. The $G_1$ dataset was used to classify the HLM data. The highest scoring subset of samples and lowest scoring subset were selected. A t-test was performed to assign significance to each probeset and identify genes that best discriminated between these subsets of the HLM training data ($p_i < 0.05/n$ for Bonferroni correction). This list of identified genes formed the new gene set $G_2$, which was used to start the process over again. After 3 iterations of classification and selection of discriminatory genes, a static group of 313 probesets was identified that were the most informative for classification of lung adenocarcinoma and used for further classification of all other data sets, seen in Table 1. This included 187 probesets from the starting 614 probesets and an additional 126 probesets. Different subgroups of genes or probesets may be useful for other tumor types.

This classifier is a majority vote classifier using probesets identified in the training set and thresholds adjusted for the data set under investigation. The individual classifiers and, if necessary, the overall classifier utilize two thresholds so that a middle ground is established which constitutes a region of uncertainty and no vote is registered with respect to the two main classes. The classifier uses a mathematical algorithm, for use on gene expression to provide a mechanism for identifying tumor samples with more ongoing mitosis. The algorithm description provides a general procedure for optimizing the genes and thresholds that will work within the framework of the data obtained from the samples. Microarray data from any platform or gene expression determined by RT-PCR is usable provided an initial algorithm training step is first performed. Gene expression data from a group of selected genes is cumulatively assessed to determine tumor samples with a high rate of mitosis and thus a higher likelihood of having a poor response to treatment. The algorithm consists of three components: the individual classifiers, the majority vote classifier, and the threshold selection. Thus, the method uses 2 established thresholds and a null vote. Of note, all classifiers started with the same set of expression summaries processed using the DChip algorithm (Li, C. & Wong, W. H. Model-based analysis of oligonucleotide arrays: expression index computation and outlier detection. *Proc Nat. Acad. Sci. U.S.A.*, 98, 31-36 (2001)), so handling of the raw data was uniform.

TERMINOLOGY

C=majority vote of individual classifiers (sum of vote by all probesets in classifier)

$c_k$=individual classifier k (a single probeset and thresholds for that probeset)

x=sample j (microarray dataset for an array from a single tumor sample)

G=set of genes used for individual classifiers (set of all probesets in classifier)

$g_{jk}$=gene expression value for sample j and probeset k

S=sign (+/−) indicating trend relative to outcome, +=high expression in Poor class, −=high expression in Good class For each $g_k$ element of G, 3 quantiles are defined by 2 threshold values, LO and HI. For this implementation of the classifier the LO threshold was set at the gene expression value closest to the $33^{rd}$ percentile and the HI threshold was set at the gene expression value closest to the $66^{th}$ percentile in the dataset under investigation. The individual classifier is then defined as $$c_k = \begin{cases} -1 * S_k & g_{jk} < LO \\ +1 * S_k & g_{jk} > HI \\ 0 & \text{otherwise} \end{cases} \quad [001]$$

This has the effect of voting −1 for samples with weak expression, +1 for samples with high expression, and 0 for samples with expression in the middle ground for probesets directly correlated to the defined classes. The vote is reversed if the gene is negatively correlated to the two classes.

The majority vote classifier is used to determine a final risk score. The sum of all individual classifiers is calculated, provided by $$C_j = \Sigma(c_{kj}) \quad [002].$$

This value can be used to develop a risk score. Alternatively, one threshold (or more) can be set to define 2 (or more) classes.

For training purposes two thresholds were set to define the extreme classes used for gene selection, as provide by $$\text{Pred}(x_j) = \begin{cases} \text{Poor} & C_j > 0.15|G| \\ \text{Good} & C_j < -0.15|G| \\ \text{Grey} & \text{otherwise} \end{cases} \quad [003]$$

0.15 was heuristically determined. A Pred value of |G| (or −1*|G|) indicates complete agreement with one class whereas small values (e.g. 0.15*|G|) indicate uncertainty in classification.

The data generated by the classifer provides a binary indication of low or high risk for each gene expression. It was noted during analysis that low and medium gene expression do not widely differ, and the classifier may be used to determine good prognosis from bad prognosis for each genetic marker (i.e. gene expression), with low and medium expression included as one group. The classifier alternatively is useful in assessing risk, determining prognosis, or discriminating between classes of tumors. In this instance, gene expression scores are cumulatively assessed. This may be performed by adding the scores of individual gene expression, in the binary −1 and 1 or tertiary −1, 0, and 1 system. The cumulative scores are then applied to a continuous score range from −G to G, where G is the number of genes scored. This cumulative score is then used to assess risk, determine prognosis, or discriminate between classes of tumors. Specifically, the score may be compared to predetermined threshold values or to cutoff thresholds. For example, good prognosis may use the lower the 33% percentile of expression, while the upper 66% designates poor prognosis. Other threshold values may be assigned.

The microarray data produced at DF was on a different scale than the data produced at the other institutions. The data was mathematically adjusted to account for the differences that exist in the DF data. The DF data, as well as the remaining data, was adjusted using two processes process. Quantile normalization was performed at the CEL file level, which several publications claim produces superior results. It also allowed later normalization on future data without having to recreate all subsequent steps of the process. A software program was developed which utilizes histogram profile of the signal intensities of each of the individual samples in the training set sampled with a fairly typical profile to serve as the reference state for the distribution of signal intensities. Using quantile normalization places the DF data on nearly the same scale as the other data sets.

To estimate signal intensity for individual genes (probesets) in the samples (array data), models based methods such as RMA and dChip can also help to correct differences between independent data sets, though the systems require all the data be processed together and significant problems arise if the data is processed separately. The data was processed together using dChip and to attempt to homogenize the data sets. Finally, the classifiers were adjusted to compensate for the data. In some classifiers the fiftieth percentile was determined in the test data. In others, an inflection point between high and low values, and for the HLM classifier the $33^{rd}$ and $66^{th}$ percentiles were identified in the test data and used to set the two threshold for the individual classifiers in the mitotic classifier. These final adjustments were needed due to problemeatic array files, which could not adequately be recognized and corrected. Of note, the adjusted thresholds may have reduced the classification algorithm's ability to stratify the data, than might have been achieved with thresholds established from the training data. Using a larger clinical data set, the thresholds can be set and no adjustment would be required for any future classification tasks.

Class Prediction or Risk Calculation for the Test Data

The thresholds for individual classifiers were reset based on the distribution of the gene expression values in each test set. The majority vote classifier was calculated to generate a score. This score exists within a continuum of values between 313 and −313, which can serve as a risk score. Alternatively, 1 or more thresholds can be set to serve as the discriminator between 2 or more classes. For a 2 class discrimination in this study the threshold was set at $C_j$>or<0.15|G|.

EXAMPLES

The estimated hazard ratios for the risk scores produced by disclosed method, with 95% confidence intervals, is shown for the two validation sets in FIG. 2. Hazard ratios substantially greater than 1.0 indicate that subjects in the validation set with high predicted risk had poor outcomes. Confidence intervals in FIG. 2 and the corresponding P-values, seen in FIG. 3, indicate the method significantly determined the method performed significantly better than expected by chance.

For performance evaluation, each predicted risk score was used as the covariate in a univariate Cox proportional hazards model, with overall survival (censored at 60 months) as the outcome variable. For graphical representation, risk scores were binned into tertiles and Kaplan-Meier estimates of the survivor function were plotted for each subgroup, seen in FIGS. 4-7. This allowed for assessment of any 'dose response' relationship. The disclosed method performed much better on sample sets containing all tumor stages compared to sample sets containing just stage I. This reflects an ability to stratify by stage even when stage is not explicitly included in the model. Further testing of the tumors classified with low mitosis, and the tumors with intermediate mitosis, seen in FIGS. 4-7, show the tumors with intermediate mitosis perform very similar to tumors with low mitosis. As such, the tumors with intermediate mitosis were included in the low mitosis tumor group.

For prediction on subjects with stage 1 disease using gene expression data only, the disclosed method gave hazard ratios exceeding 1 for both validation sets. The classifier used a binary indication of low or high risk for each gene expression. For example, in the MSK all stages prediction, patients 19L, 37L_REP and 67L are correctly predicted to die early whereas 41L is predicted to be low risk and does live for more than 5 years.

As another performance measure, the concordance probability estimate (CPE) was calculated to measure agreement between subject outcomes and predicted risk scores (Gonen, M. & Heller, G. Concordance probability and discriminatory power in proportional hazards regression. *Biometrika* 92:4, 965-970 (2005)). The CPE estimates the concordance probability, which is the probability that, for a given pair of subjects selected at random from the study population, the subject with better prognosis has a better outcome. CPE values close to 0.5 indicate no concordance (poor predictivity); CPE values approaching 1.0 indicate strong concordance (good predictivity). On the basis of these measures, the method performed consistently well, showing moderate concordance as seen in FIG. 3.

The CAN/DF data set differed from the other datasets in that it lacked stage 3 samples. To give a realistic evaluation of how a prognostic method might be used in practice, the combined data from HLM was used as the training set, with MSK held out as a similar but external validation set and the CAN/DF data held out as a second and more challenging external validation set.

Figures 7, 8:
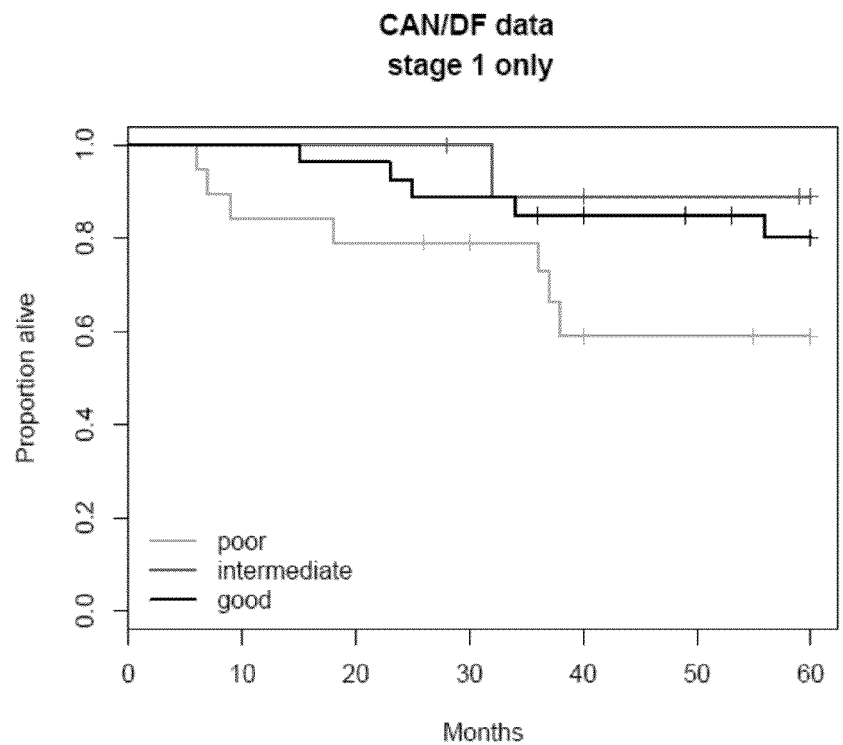
FIG. 7 is a graph of Kaplan-Meier estimates of survivor function for the CAN/DF validation set using only stage I tumors. Low scores correspond to the lowest predicted risk and high scores correspond to the greatest predicted risk.
FIG. 8 is a table of ROC data of sensitivity and specificity values.
Figure 9:
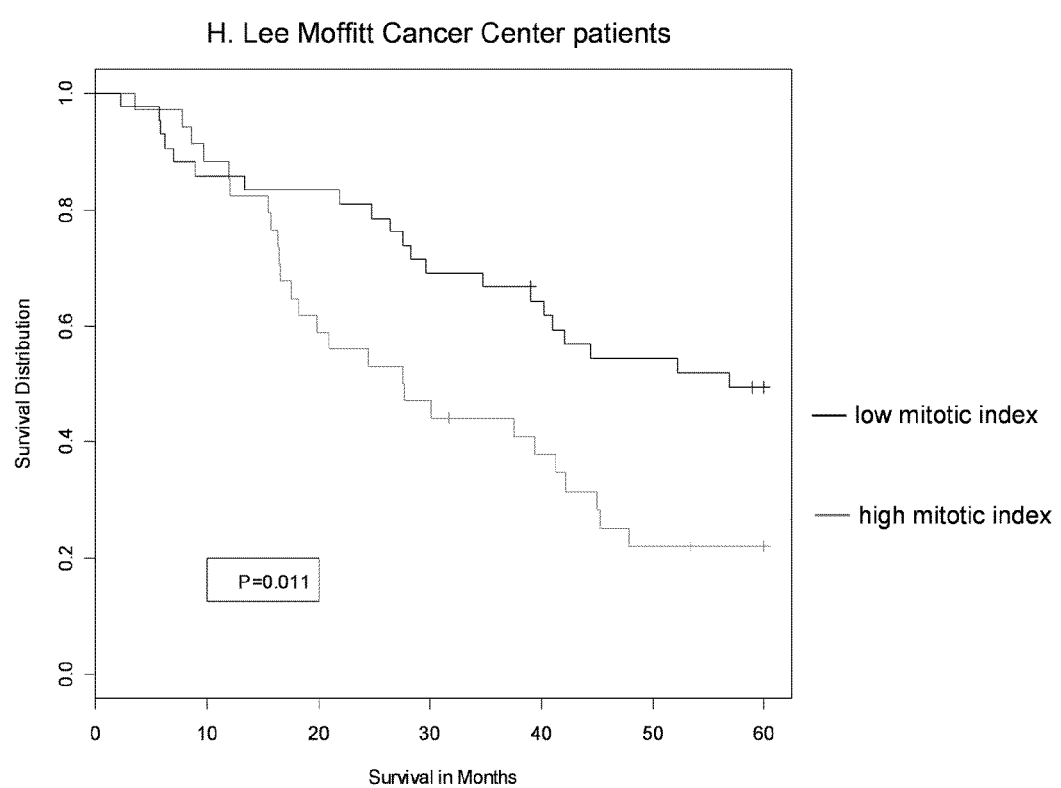
FIG. 9 is a graph of survivor function estimates for the HLM gene set, with the data separated into 2 groups; patients with good prognosis (low mitotic indices) versus poor prognosis (high mitotic indices).

For 3-year survival, receiver operating characteristics (ROC) were constructed for the categorical predictor, seen in FIG. 8. Sensitivity and specificity were calculated using Bayes' theorem and Kaplan-Meier estimates of the survivor function and hazard function to appropriately handle censoring. To calculate the sensitivity for a rule based on a given risk-score cutoff k, $P(R>k|T<t)=P(T<t|R>k)*P(R>k)/P(T<t)$ was expressed, where T is the survival time, t=36 months is the follow-up time we used for this analysis, and R is a risk score. The terms $P(T<t)$ and $P(T<t|R>k)$ can be estimated using the Kaplan-Meier procedure, and $P(R>k)$ is estimated directly with its empirical probability. When the conditioning sets {R>k} (for sensitivity) and {R<k} (for specificity) become small, the Kaplan-Meier estimates are very unstable. Split points were excluded where either of these sets contains fewer than five values. Similarly, the specificity $P(R<k|T>t)=P(T>t|R<k)*P(R<k)/P(T>t)$ was estimated.

Example 2

Majority Vote Classifier

Using the majority vote classifier described above, a training algorithm was used for calibration. A gene set, G, was selected from which the entire classification process is performed. The initial 614 mitosis-related probesets, the reference gene set M, were considered by the algorithm. Gene set, G, is compared to reference gene set M using the majority vote classifier and setting G equal to set M. This generates two groups: genes with high mitotic indices and those with low mitotic indices. Samples with intermediate expression levels are removed, so that at test can be performed between the classified samples in the high mitotic group and low mitotic group.

n=number of genes overall, or 22,000 in the present example;

$S_i$=sign($t_i$)

The genes are individually separated into two groups for the expression of gene i, Xit=good, Xit=poor. At test is performed on the two gene expression groups, Xit=good, Xit=poor, resulting in ti, followed by significance testing to determine a p value, pi for gene/probeset i.

G was selected such that G=gi:pi<0.05/n (the p value subjected to Bonferroni correction). The new G serves as the set of genes/probesets to reclassify the samples. The process iterates between definition of the low and high mitotic index groups (classification on the training set) and identifying the genes/probesets that make up the set G. After 3 iterations on the HLM data, there were 313 probesets identified within the classifier and used for prediction on the test sets.

Figure 10:
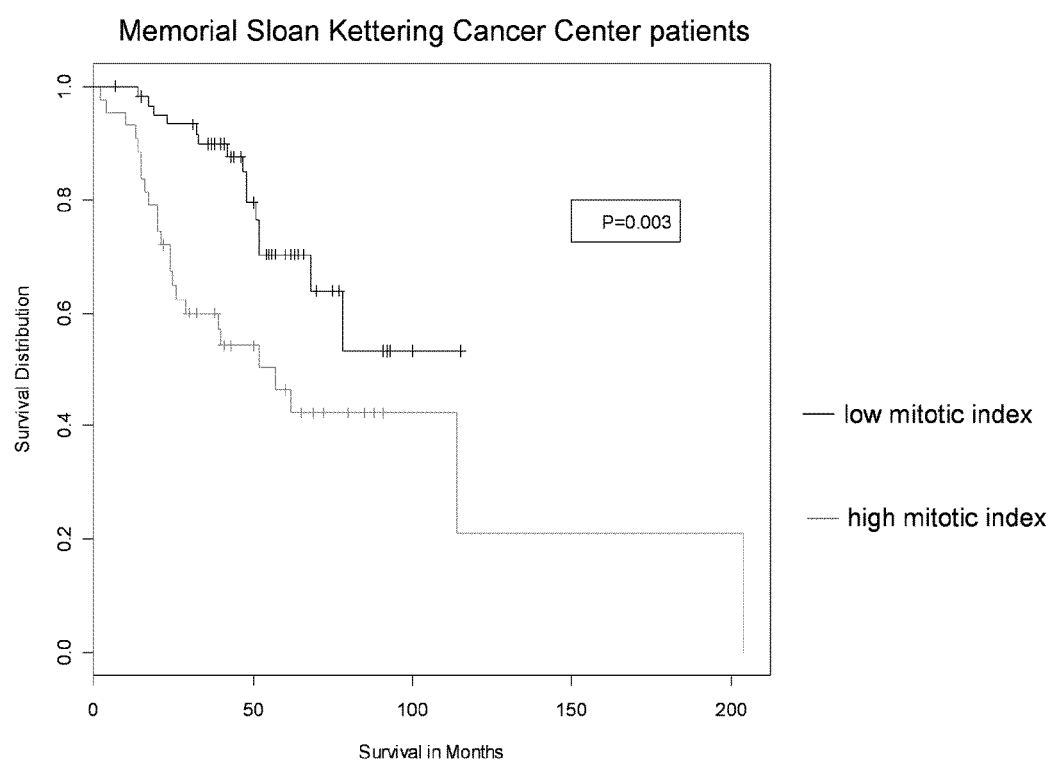
FIG. 10 is a graph of survivor function estimates for the DF gene set, with the data separated into 2 groups; patients with good prognosis (low mitotic indices) versus poor prognosis (high mitotic indices).
Figure 11:
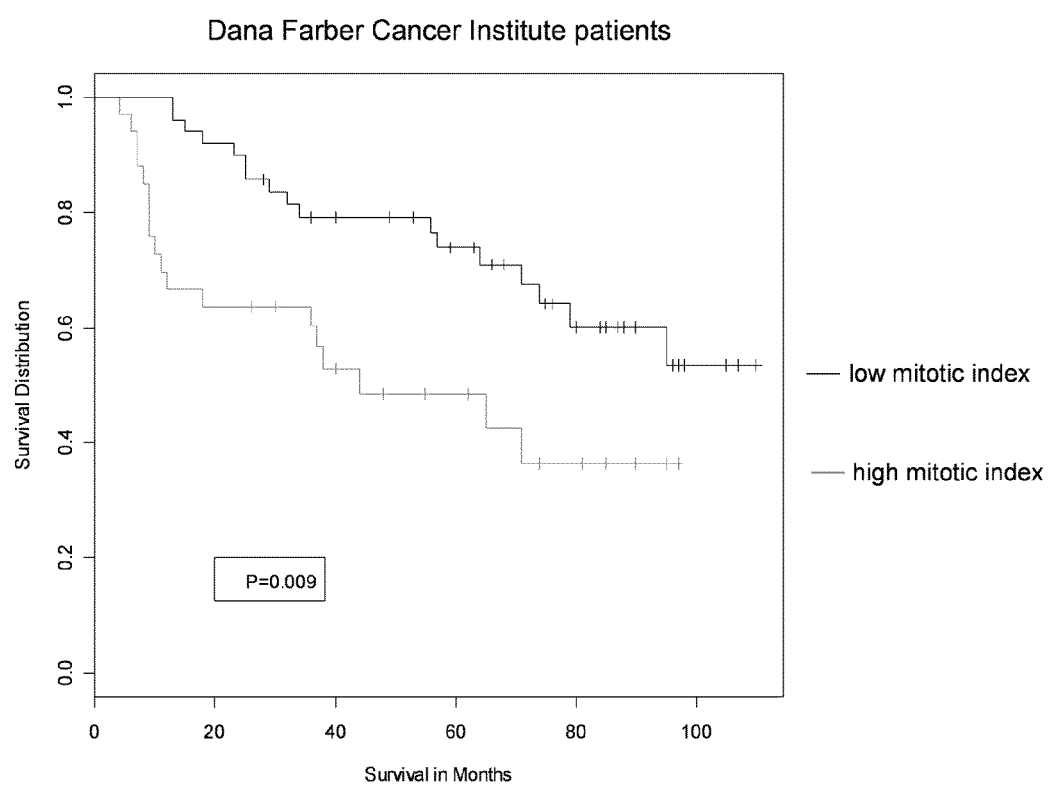
FIG. 11 is a graph of survivor function estimates for the MSK gene set, with the data separated into 2 groups; patients with good prognosis (low mitotic indices) versus poor prognosis (high mitotic indices).
Figure 12:
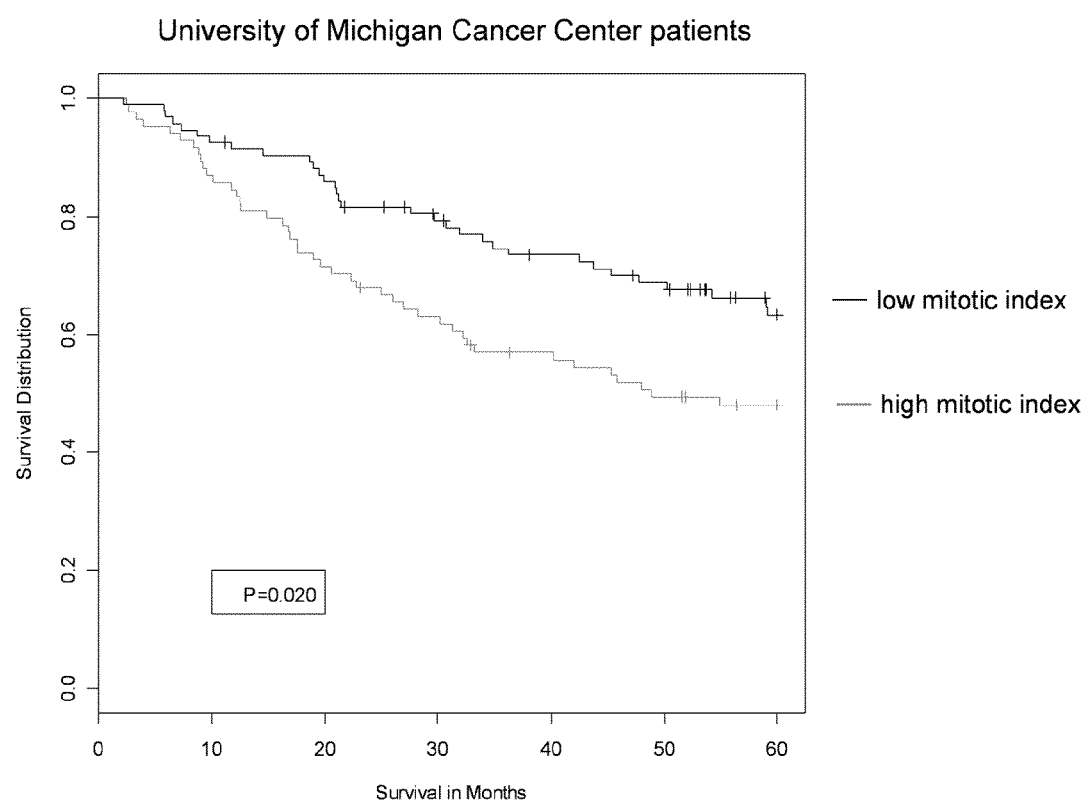
FIG. 12 is a graph of survivor function estimates for the UMC gene set, with the data separated into 2 groups; patients with good prognosis (low mitotic indices) versus poor prognosis (high mitotic indices).

The data from the gene sets were analyzed using the two classes, good prognosis (low mitotic index) versus bad prognosis (high mitotic index), seen in FIGS. 9-12. The disclosed method successfully distinguished between the prognosis classes, with tumors classified with low mitotic indices exhibiting significantly higher survival distributions. Applying the method to the test gene sets shows the method stratifies patient prognosis after normalizing expression values. The HLM gene set, patients with good prognosis (low mitotic indices) showed initial higher mortality, possibly due to post-treatment complications, seen in FIG. 9. After this initial period, these patients exhibited increased survival, with approximately 50% of patients surviving to the conclusion of the study, compared to about 25% of the patients diagnosed with poor prognosis. DF and MSK patient data evidence better concordance between the prognosis and patient mortality, as seen in FIGS. 10 and 11. In both data sets, patients with good prognosis had a much higher likelihood of survival out to over 100 months post-treatment. Data for UMC showed less variation between good and poor prognosis, mainly due to increased survival of patients with high mitotic indices, seen in FIG. 12. However, patients with low mitotic indices possessed a substantial increase in survival.

Each reference cited in the preceding disclosure is herein expressly incorporated by reference in its entirety, to the same extent as if the reference was incorporated by reference individually.

In the preceding specification, all documents, acts, or information disclosed does not constitute an admission that the document, act, or information or any combination thereof was publicly available, known to the public, part of the general knowledge in the art, or was known to be relevant to solve any problem at the time of priority.

While there has been described and illustrated specific embodiments of a gene expression classifier, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween. Now that the invention has been described,

TABLE 1

| | Probe ID | GenBank ID | Entrez Gene ID | Gene Symbol | Gene description |
|---|---|---|---|---|---|
| | | | | | Probeset data information |
| 1 | 1053_at | NM_002914.3 | e | RFC2 | replication factor C (activator 1) 2, 40 kDa |
| 1 | 200783_s_at | NM_203399.1 | 3925 | STMN1 | stathmin 1/oncoprotein 18 |
| 1 | 200853_at | NM_002106.3 | 3015 | H2AFZ | H2A histone family, member Z |
| 1 | 201088_at | NM_002266.2 | 3838 | KPNA2 | karyopherin alpha 2 (RAG cohort 1, importin alpha 1) |
| 1 | 201090_x_at | NM_006082.2 | 10376 | | |
| 1 | 201091_s_at | NM_007276.3 | 11335 | TUBA1B CBX3 | tubulin, alpha 1b chromobox homolog 3 (HP1 gamma homolog, *Drosophila*) |
| 1 | 201111_at | NM_001316.2 | 1434 | CSE1L | CSE1 chromosome segregation 1-like (yeast) |
| 1 | 201112_s_at | NM_001316.2 | 1434 | CSE1L | CSE1 chromosome segregation 1-like (yeast) |

TABLE 1-continued

Probeset data information

| Probe ID | GenBank ID | Entrez Gene ID | Gene Symbol | Gene description |
|---|---|---|---|---|
| 1 201202_at | NM_182649.1 | 5111 | PCNA | proliferating cell nuclear antigen |
| 1 201291_s_at | NM_001067.2 | 7153 | TOP2A | topoisomerase (DNA) II alpha 170 kDa |
| 1 201292_at | NM_001067.2 | 7153 | TOP2A | topoisomerase (DNA) II alpha 170 kDa |
| 1 201477_s_at | NM_001033.2 | 6240 | RRM1 | ribonucleotide reductase M1 polypeptide |
| 1 201479_at | NM_001363.2 | 1736 | DKC1 | dyskeratosis congenita 1, dyskerin |
| 1 201555_at | NM_002388.3 | 4172 | MCM3 | MCM3 minichromosome maintenance deficient 3 (*S. cerevisiae*) |
| 1 201584_s_at | NM_005804.2 | 10212 | DDX39 | DEAD (Asp-Glu-Ala-Asp) box polypeptide 39 |
| 1 201697_s_at | NM_001379.1 | 1786 | DNMT1 | DNA (cytosine-5-)-methyltransferase 1 |
| 1 201710_at | NM_002466.2 | 4605 | MYBL2 | v-myb myeloblastosis viral oncogene homolog (avian)-like 2 |
| 1 201770_at | NM_004596.3 | 6626 | SNRPA | small nuclear ribonucleoprotein polypeptide A |
| 1 201774_s_at | NM_014865.2 | 9918 | NCAPD2 | non-SMC condensin I complex, subunit D2 |
| 1 201890_at | NM_001034 | 6241 | RRM2 | ribonucleotide reductase M2 polypeptide |
| 1 201896_s_at | NM_001005290.2 | 84722 | PSRC1 | proline/serine-rich coiled-coil 1 |
| 1 201897_s_at | NM_001826.1 | 1163 | CKS1B | CDC28 protein kinase regulatory subunit 1B |
| 1 201930_at | NM_005915.4 | 4175 | MCM6 | MCM6 minichromosome maintenance deficient 6 (MIS5 homolog, *S. pombe*) (*S. cerevisiae*) |
| 1 202094_at | NM_001012270.1 | 332 | BIRC5 | baculoviral IAP repeat-containing 5 (survivin) |
| 1 202095_s_at | NM_001012271.1 | 332 | BIRC5 | baculoviral IAP repeat-containing 5 (survivin) |
| 1 202107_s_at | NM_004526.2 | 4171 | MCM2 | MCM2 minichromosome maintenance deficient 2, mitotin (*S. cerevisiae*) |
| 1 202153_s_at | NM_012346.3 | 23636 | NUP62 | nucleoporin 62 kDa |
| 1 202338_at | NM_003258.1 | 7083 | TK1 | thymidine kinase 1, soluble |
| 1 202483_s_at | NM_002882.2 | 5902 | RANBP1 | RAN binding protein 1 |
| 1 202503_s_at | NM_014736.4 | 9768 | KIAA0101 | KIAA0101 |
| 1 202580_x_at | NM_021953.2 | 2305 | FOXM1 | forkhead box M1 |
| 1 202589_at | NM_001071.1 | 7298 | TYMS | thymidylate synthetase |
| 1 202715_at | NM_004341.3 | 790 | CAD | carbamoyl-phosphate synthetase 2, aspartate transcarbamylase, and dihydroorotase |
| 1 202726_at | NM_000234.1 | 3978 | LIG1 | ligase I, DNA, ATP-dependent |
| 1 202779_s_at | NM_014501.1 | 27338 | UBE2S | ubiquitin-conjugating enzyme E2S |
| 1 202870_s_at | NM_001255.1 | 991 | CDC20 | CDC20 cell division cycle 20 homolog (*S. cerevisiae*) |
| 1 202904_s_at | NM_012322.1 | 23658 | LSM5 | LSM5 homolog, U6 small nuclear RNA associated (*S. cerevisiae*) |
| 1 202911_at | NM_000179.1 | 2956 | MSH6 | mutS homolog 6 (*E. coli*) |
| 1 202954_at | NM_181800.1 | 11065 | UBE2C | ubiquitin-conjugating enzyme E2C |
| 1 203022_at | NM_006397.2 | 10535 | RNASEH2A | ribonuclease H2, large subunit |
| 1 203046_s_at | NM_003920.2 | 8914 | TIMELESS | timeless homolog (*Drosophila*) |
| 1 203145_at | NM_006461.3 | 10615 | SPAG5 | sperm associated antigen 5 |
| 1 203209_at | NM_181578.1 | 5985 | RFC5 | replication factor C (activator 1) 5, 36.5 kDa |
| 1 203210_s_at | NM_007370.3 | 5985 | RFC5 | replication factor C (activator 1) 5, 36.5 kDa |
| 1 203213_at | NM_001786 | 983 | CDC2 | cell division cycle 2, G1 to S and G2 to M |
| 1 203214_x_at | NM_001786.2 | 983 | CDC2 | cell division cycle 2, G1 to S and G2 to M |
| 1 203270_at | NM_012145.2 | 1841 | DTYMK | deoxythymidylate kinase (thymidylate kinase) |
| 1 203362_s_at | NM_002358.2 | 4085 | MAD2L1 | MAD2 mitotic arrest deficient-like 1 (yeast) |
| 1 203418_at | NM_001237.2 | 890 | CCNA2 | cyclin A2 |
| 1 203432_at | NM_003276 | 7112 | TMPO | Caution, check this probeset carefully. This probeset may detect an extended transcript of thymopoietin |
| 1 203554_x_at | NM_004219.2 | 9232 | PTTG1 | pituitary tumor-transforming 1 |
| 1 203696_s_at | NM_002914.3 | 5982 | RFC2 | replication factor C (activator 1) 2, 40 kDa |
| 1 203755_at | NM_001211.4 | 701 | BUB1B | BUB1 budding uninhibited by benzimidazoles 1 homolog beta (yeast) |
| 1 203764_at | NM_014750.3 | 9787 | DLG7 | discs, large homolog 7 (*Drosophila*) |
| 1 203832_at | NM_003095.2 | 6636 | SNRPF | small nuclear ribonucleoprotein polypeptide F |
| 1 203856_at | NM_003384.2 | 7443 | VRK1 | vaccinia related kinase 1 |
| 1 203967_at | NM_001254.3 | 990 | CDC6 | CDC6 cell division cycle 6 homolog (*S. cerevisiae*) |
| 1 203968_s_at | NM_001254.3 | 990 | CDC6 | CDC6 cell division cycle 6 homolog (*S. cerevisiae*) |
| 1 203976_s_at | NM_005483.2 | 10036 | CHAF1A | chromatin assembly factor 1, subunit A (p150) |
| 1 204023_at | NM_181573.1 | 5984 | RFC4 | replication factor C (activator 1) 4, 37 kDa |
| 1 204026_s_at | NM_001005413.1 | 11130 | ZWINT | ZW10 interactor |
| 1 204033_at | NM_004237.2 | 9319 | TRIP13 | thyroid hormone receptor interactor 13 |
| 1 204092_s_at | NM_198433.1 | 6790 | STK6 | serine/threonine kinase 6 |
| 1 204126_s_at | NM_003504.3 | 8318 | CDC45L | CDC45 cell division cycle 45-like (*S. cerevisiae*) |
| 1 204127_at | NM_002915 | 5983 | RFC3 | replication factor C (activator 1) 3, 38 kDa |
| 1 204128_s_at | NM_002915 | 5983 | RFC3 | replication factor C (activator 1) 3, 38 kDa |

TABLE 1-continued

Probeset data information

| Probe ID | GenBank ID | Entrez Gene ID | Gene Symbol | Gene description |
|---|---|---|---|---|
| 1 204162_at | NM_006101.1 | 10403 | KNTC2 | kinetochore associated 2 |
| 1 204170_s_at | NM_001827.1 | 1164 | CKS2 | CDC28 protein kinase regulatory subunit 2 |
| 1 204240_s_at | NM_006444 | 10592 | SMC2L1 | SMC2 structural maintenance of chromosomes 2-like 1 (yeast) |
| 1 204244_s_at | NM_006716.3 | 10926 | DBF4 | DBF4 homolog (S. cerevisiae) |
| 1 204318_s_at | NM_016426.4 | 51512 | GTSE1 | G-2 and S-phase expressed 1 |
| 1 204407_at | NM_003594.3 | 8458 | TTF2 | transcription termination factor, RNA polymerase II |
| 1 204444_at | NM_004523.2 | 3832 | KIF11 | kinesin family member 11 |
| 1 204492_at | NM_014783.2 | 9824 | ARHGAP11A | Rho GTPase activating protein 11A |
| 1 204558_at | NM_003579.2 | 8438 | RAD54L | RAD54-like (S. cerevisiae) |
| 1 204641_at | NM_002497.2 | 4751 | NEK2 | NIMA (never in mitosis gene a)-related kinase 2 |
| 1 204709_s_at | NM_138555.1 | 9493 | KIF23 | kinesin family member 23 |
| 1 204766_s_at | NM_198950.1 | 4521 | NUDT1 | nudix (nucleoside diphosphate linked moiety X)-type motif 1 |
| 1 204767_s_at | NM_004111.4 | 2237 | FEN1 | flap structure-specific endonuclease 1 |
| 1 204768_s_at | NM_004111.4 | 2237 | FEN1 | flap structure-specific endonuclease 1 |
| 1 204822_at | NM_003318.3 | 7272 | TTK | TTK protein kinase |
| 1 204825_at | NM_014791.2 | 9833 | MELK | maternal embryonic leucine zipper kinase |
| 1 204886_at | NM_014264 | 10733 | STK18 | serine/threonine kinase 18 |
| 1 204887_s_at | NM_014264.2 | 10733 | PLK4 | polo-like kinase 4 (Drosophila) |
| 1 204947_at | NM_005225.1 | 1869 | E2F1 | E2F transcription factor 1 |
| 1 204962_s_at | NM_001809 | 1058 | CENPA | centromere protein A, 17 kDa |
| 1 205046_at | NM_001813.2 | 1062 | CENPE | centromere protein E, 312 kDa |
| 1 205053_at | NM_000946.2 | 5557 | PRIM1 | primase, polypeptide 1, 49 kDa |
| 1 205085_at | NM_004153.2 | 4998 | ORC1L | origin recognition complex, subunit 1-like (yeast) |
| 1 205167_s_at | NM_022809.1 | 995 | CDC25C | cell division cycle 25C |
| 1 205393_s_at | NM_001274.2 | 1111 | CHEK1 | CHK1 checkpoint homolog (S. pombe) |
| 1 205394_at | NM_001274.2 | 1111 | CHEK1 | CHK1 checkpoint homolog (S. pombe) |
| 1 205644_s_at | NM_003096.2 | 6637 | SNRPG | small nuclear ribonucleoprotein polypeptide G |
| 1 206055_s_at | NM_003090.2 | 6627 | SNRPA1 | small nuclear ribonucleoprotein polypeptide A' |
| 1 206102_at | NM_021067 | 9837 | KIAA0186 | KIAA0186 gene product |
| 1 206364_at | NM_014875.1 | 9928 | KIF14 | kinesin family member 14 |
| 1 206550_s_at | NM_153485.1 | 9631 | NUP155 | nucleoporin 155 kDa |
| 1 207165_at | NM_012484.1 | 3161 | HMMR | hyaluronan-mediated motility receptor (RHAMM) |
| 1 207828_s_at | NM_016343.3 | 1063 | CENPF | centromere protein F, 350/400 ka (mitosin) |
| 1 208079_s_at | NM_003600.2 | 6790 | STK6 | serine/threonine kinase 6 |
| 1 208696_at | NM_012073.3 | 22948 | CCT5 | chaperonin containing TCP1, subunit 5 (epsilon) |
| 1 208766_s_at | NM_005826.2 | 10236 | HNRPR | heterogeneous nuclear ribonucleoprotein R |
| 1 208795_s_at | NM_182776.1 | 4176 | MCM7 | MCM7 minichromosome maintenance deficient 7 (S. cerevisiae) |
| 1 208808_s_at | NM_002129.2 | 3148 | HMGB2 | high-mobility group box 2 |
| 1 208821_at | NM_003091.3 | 6628 | SNRPB | small nuclear ribonucleoprotein polypeptides B and B1 |
| 1 209026_x_at | NM_178014.2 | 203068 | TUBB | tubulin, beta |
| 1 209053_s_at | NM_014919.1 | 7468 | WHSC1 | Wolf-Hirschhorn syndrome candidate 1 |
| 1 209251_x_at | NM_032704.2 | 84790 | TUBA6 | tubulin, alpha 6 |
| 1 209408_at | NM_006845.2 | 11004 | KIF2C | kinesin family member 2C |
| 1 209464_at | NM_004217 | 9212 | AURKB | aurora kinase B |
| 1 209642_at | NM_004336.2 | 699 | BUB1 | BUB1 budding uninhibited by benzimidazoles |
| 1 209680_s_at | NM_002263.2 | 3833 | KIFC1 | kinesin family member C1 |
| 1 209714_s_at | NM_005192.2 | 1033 | CDKN3 | cyclin-dependent kinase inhibitor 3 (CDK2-associated dual specificity phosphatase) |
| 1 209773_s_at | NM_001034.1 | 6241 | RRM2 | ribonucleotide reductase M2 polypeptide |
| 1 $$_s_at | NM_030928.1 | 81620 | CDT1 | chromatin licensing and DNA replication factor 1 |
| 1 209891_at | NM_020675.3 | 57405 | SPBC25 | spindle pole body component 25 homolog (S. cerevisiae) |
| 1 210052_s_at | NM_012112.4 | 22974 | TPX2 | TPX2, microtubule-associated, homolog (Xenopus laevis) |
| 1 210559_s_at | NM_001786.2 | 983 | CDC2 | cell division cycle 2, G1 to S and G2 to M |
| 1 210766_s_at | NM_001316.2 | 1434 | CSE1L | CSE1 chromosome segregation 1-like (yeast) |
| 1 210983_s_at | NM_005916.3 | 4176 | MCM7 | MCM7 minichromosome maintenance deficient 7 (S. cerevisiae) |
| 1 211058_x_at | NM_006082.2 | 10376 | TUBA1B | tubulin, alpha 1b |
| 1 211072_x_at | NM_006082.2 | 10376 | TUBA1B | tubulin, alpha 1b |
| 1 211080_s_at | NM_002497.2 | 4751 | NEK2 | NIMA (never in mitosis gene a)-related kinase 2 |
| 1 211375_s_at | NM_012218.2 | 3609 | ILF3 | interleukin enhancer binding factor 3, 90 kDa |
| 1 211519_s_at | NM_006845.2 | 11004 | KIF2C | kinesin family member 2C |
| 1 211714_x_at | NM_178014.2 | 203068 | TUBB | tubulin, beta |
| 1 211747_s_at | NM_012322.1 | 23658 | LSM5 | LSM5 homolog, U6 small nuclear RNA associated (S. cerevisiae) |

TABLE 1-continued

Probeset data information

| | Probe ID | GenBank ID | Entrez Gene ID | Gene Symbol | Gene description |
|---|---|---|---|---|---|
| 1 | 211750_x_at | NM_032704.2 | 84790 | TUBA6 | tubulin, alpha 6 |
| 1 | 211762_s_at | NM_002266.2 | 3838 | KPNA2 | karyopherin alpha 2 (RAG cohort 1, importin alpha 1) |
| 1 | 212020_at | NM_002417 | 4288 | MKI67 | antigen identified by monoclonal antibody Ki-67 |
| 1 | 212022_s_at | NM_002417 | 4288 | MKI67 | antigen identified by monoclonal antibody Ki-67 |
| 1 | 212023_s_at | NM_002417 | 4288 | MKI67 | antigen identified by monoclonal antibody Ki-67 |
| 1 | 212247_at | NM_015135.1 | 23165 | NUP205 | nucleoporin 205 kDa |
| 1 | 212639_x_at | NM_006082.2 | 10376 | TUBA1B | tubulin, alpha 1b |
| 1 | 212949_at | NM_015341.3 | 23397 | BRRN1 | barren homolog 1 (Drosophila) |
| 1 | 213007_at | NM_018193.2 | 55215 | KIAA1794 | KIAA1794 |
| 1 | 213008_at | NM_018193.2 | 55215 | KIAA1794 | KIAA1794 |
| 1 | 213088_s_at | NM_015190.3 | 23234 | DNAJC9 | DnaJ (Hsp40) homolog, subfamily C, member 9 |
| 1 | 213175_s_at | NM_003091.3 | 6628 | SNRPB | small nuclear ribonucleoprotein polypeptides B and B1 |
| 1 | 213226_at | | 890 | CCNA2 | Caution, check this probeset carefully. This probeset may detect an extended transcript or alternate termination site of cyclin A2 |
| 1 | 213646_x_at | NM_006082.2 | 10376 | TUBA1B | tubulin, alpha 1b |
| 1 | 213911_s_at | NM_002106.3 | 3015 | H2AFZ | H2A histone family, member Z |
| 1 | 213951_s_at | NM_013290.3 | 29893 | PSMC3IP | PSMC3 interacting protein |
| 1 | 214426_x_at | NM_005483.2 | 10036 | CHAF1A | chromatin assembly factor 1, subunit A (p150) |
| 1 | 214431_at | NM_003875.2 | 8833 | GMPS | guanine monphosphate synthetase |
| 1 | 214710_s_at | NM_031966.2 | 891 | CCNB1 | cyclin B1 |
| 1 | 214804_at | NM_006733 | 2491 | FSHPRH1 | Caution, check this probeset carefully. This probeset may detect an extended transcript of FSH primary response (LRPR1 homolog, rat) 1 |
| 1 | 216237_s_at | NM_006739.2 | 4174 | MCM5 | MCM5 minichromosome maintenance deficient 5, cell division cycle 46 (S. cerevisiae) |
| 1 | 216952_s_at | NM_032737.2 | 84823 | LMNB2 | lamin B2 |
| 1 | 217714_x_at | NM_005563 | 3925 | STMN1 | stathmin 1/oncoprotein 18 |
| 1 | 218009_s_at | NM_003981.2 | 9055 | PRC1 | protein regulator of cytokinesis 1 |
| 1 | 218039_at | NM_016359.2 | 51203 | NUSAP1 | nucleolar and spindle associated protein 1 |
| 1 | 218073_s_at | NM_018087.3 | 55706 | TMEM48 | transmembrane protein 48 |
| 1 | 218115_at | NM_018154.2 | 55723 | ASF1B | ASF1 anti-silencing function 1 homolog B (S. cerevisiae) |
| 1 | 218252_at | NM_018204.2 | 26586 | CKAP2 | cytoskeleton associated protein 2 |
| 1 | 218308_at | NM_006342.1 | 10460 | TACC3 | transforming, acidic coiled-coil containing protein 3 |
| 1 | 218355_at | NM_012310.2 | 24137 | KIF4A | kinesin family member 4A |
| 1 | 218497_s_at | NM_002936.3 | 246243 | RNASEH1 | ribonuclease H1 |
| 1 | 218542_at | NM_018131.3 | 55165 | CEP55 | centrosomal protein 55 kDa |
| 1 | 218585_s_at | NM_016448.1 | 51514 | DTL | denticleless homolog (Drosophila) |
| 1 | 218662_s_at | NM_022346.3 | 64151 | NCAPG | non-SMC condensin I complex, subunit G |
| 1 | 218663_at | NM_022346.3 | 64151 | NCAPG | non-SMC condensin I complex, subunit G |
| 1 | 218726_at | NM_018410.3 | 55355 | DKFZp762E1312 | hypothetical protein DKFZp762E1312 |
| 1 | 218755_at | NM_005733.1 | 10112 | KIF20A | kinesin family member 20A |
| 1 | 218782_s_at | NM_014109.2 | 29028 | ATAD2 | ATPase family, AAA domain containing 2 |
| 1 | 218875_s_at | NM_012177.2 | 26271 | FBXO5 | F-box protein 5 |
| 1 | 218883_s_at | NM_024629.2 | 79682 | MLF1IP | MLF1 interacting protein |
| 1 | 219148_at | NM_018492.2 | 55872 | PBK | PDZ binding kinase |
| 1 | 219162_s_at | NM_170739.1 | 65003 | MRPL11 | mitochondrial ribosomal protein L11 |
| 1 | 219306_at | NM_020242.1 | 56992 | KIF15 | kinesin family member 15 |
| 1 | 219493_at | NM_024745.2 | 79801 | SHCBP1 | SHC SH2-domain binding protein 1 |
| 1 | 219512_at | NM_024918.2 | 79980 | C20orf172 | chromosome 20 open reading frame 172 |
| 1 | 219588_s_at | AK092008.1 | 54892 | LUZP5 | leucine zipper protein 5 |
| 1 | 219650_at | NM_001009954.1 | 54821 | FLJ20105 | FLJ20105 protein |
| 1 | 219787_s_at | NM_018098.4 | 1894 | ECT2 | epithelial cell transforming sequence 2 oncogene |
| 1 | 219978_s_at | NM_016359.2 | 51203 | NUSAP1 | nucleolar and spindle associated protein 1 |
| 1 | 220060_s_at | NM_017915.2 | 55010 | C12orf48 | chromosome 12 open reading frame 48 |
| 1 | 220239_at | AF111113.1 | 55975 | KLHL7 | Caution, check this probeset carefully. This probeset may detect an unusual splice variant, alternate termination site, or alternate start site of kelch-like 7 (Drosophila) |
| 1 | 220651_s_at | NM_018518.3 | 55388 | MCM10 | MCM10 minichromosome maintenance deficient 10 (S. cerevisiae) |
| 1 | 221258_s_at | NM_031217.2 | 81930 | KIF18A | kinesin family member 18A |
| 1 | 221436_s_at | NM_031299.3 | 83461 | CDCA3 | cell division cycle associated 3 |
| 1 | 221520_s_at | NM_018101.2 | 55143 | CDCA8 | cell division cycle associated 8 |
| 1 | 221677_s_at | NM_017613.2 | 29980 | DONSON | downstream neighbor of SON |
| 1 | 222036_s_at | NM_005914 | 4173 | MCM4 | MCM4 minichromosome maintenance deficient 4 (S. cerevisiae) |
| 1 | 222039_at | BC048263.1 | 146909 | LOC146909 | hypothetical protein LOC146909 |
| 1 | 222077_s_at | NM_013277.2 | 29127 | RACGAP1 | Rac GTPase activating protein 1 |
| 1 | 38158_at | NM_012291.3 | 9700 | ESPL1 | extra spindle poles like 1 (S. cerevisiae) |
| 0 | 200799_at | NM_005345.4 | 3303 | HSPA1A | heat shock 70 kDa protein 1A |
| 0 | 200800_s_at | NM_005345.4 | 3303 | HSPA1A | heat shock 70 kDa protein 1A |
| 0 | 200913_at | NM_177983.1 | 5496 | PPM1G | protein phosphatase 1G (formerly 2C), magnesium-dependent, gamma isoform |

TABLE 1-continued

Probeset data information

| Probe ID | GenBank ID | Entrez Gene ID | Gene Symbol | Gene description |
|---|---|---|---|---|
| 0 200934_at | NM_003472 | 7913 | DEK | DEK oncogene (DNA binding) |
| 0 201475_x_at | NM_004990.2 | 4141 | MARS | methionine-tRNA synthetase |
| 0 201478_s_at | NM_001363.2 | 1736 | DKC1 | dyskeratosis congenita 1, dyskerin |
| 0 201535_at | NM_007106.2 | 5412 | UBL3 | ubiquitin-like 3 |
| 0 201761_at | NM_001040409.1 | 10797 | MTHFD2 | methylenetetrahydrofolate dehydrogenase (NADP+ dependent) 2, methenyltetrahydrofolate cyclohydrolase |
| 0 201762_s_at | NM_002818.2 | 5721 | PSME2 | proteasome (prosome, macropain) activator subunit 2 (PA28 beta) |
| 0 201833_at | NM_001527.1 | 3066 | HDAC2 | histone deacetylase 2 |
| 0 202105_at | NM_001551.2 | 3476 | IGBP1 | immunoglobulin (CD79A) binding protein 1 |
| 0 202633_at | NM_007027.2 | 11073 | TOPBP1 | topoisomerase (DNA) II binding protein 1 |
| 0 202666_s_at | AB015907.1 | 86 | ACTL6A | actin-like 6A |
| 0 202738_s_at | NM_000293.1 | 5257 | PHKB | phosphorylase kinase, beta |
| 0 202754_at | NM_015361.2 | 23518 | R3HDM1 | R3H domain containing 1 |
| 0 202854_at | NM_000194.1 | 3251 | HPRT1 | hypoxanthine phosphoribosyltransferase 1 (Lesch-Nyhan syndrome) |
| 0 202983_at | NM_003071.2 | 6596 | SMARCA3 | SWI/SNF related, matrix associated, actin dependent regulator of chromatin, subfamily a, member 3 |
| 0 203087_s_at | NM_004520.1 | 3796 | KIF2 | kinesin heavy chain member 2 |
| 0 203276_at | NM_005573.2 | 4001 | LMNB1 | lamin B1 |
| 0 203302_at | NM_000788.1 | 1633 | DCK | deoxycytidine kinase |
| 0 203358_s_at | NM_004456.3 | 2146 | EZH2 | enhancer of zeste homolog 2 (*Drosophila*) |
| 0 203414_at | NM_012329.2 | 23531 | MMD | monocyte to macrophage differentiation-associated |
| 0 203420_at | NM_016255.1 | 51439 | FAM8A1 | family with sequence similarity 8, member A1 |
| 0 203693_s_at | NM_001949.2 | 1871 | E2F3 | E2F transcription factor 3 |
| 0 204146_at | NM_006479.2 | 10635 | RAD51AP1 | RAD51 associated protein 1 |
| 0 204165_at | NM_001024935.1 | 8936 | WASF1 | WAS protein family, member 1 |
| 0 204315_s_at | NM_016426.4 | 51512 | GTSE1 | G-2 and S-phase expressed 1 |
| 0 204317_at | NM_016426.4 | 51512 | GTSE1 | G-2 and S-phase expressed 1 |
| 0 204510_at | NM_003503.2 | 8317 | CDC7 | CDC7 cell division cycle 7 (*S. cerevisiae*) |
| 0 204649_at | NM_005480.2 | 10024 | TROAP | trophinin associated protein (tastin) |
| 0 204695_at | NM_201567.1 | 993 | CDC25A | cell division cycle 25A |
| 0 204727_at | AY517556.1 | 11169 | WDHD1 | WD repeat and HMG-box DNA binding protein 1 |
| 0 204728_s_at | NM_001008396.1 | 11169 | WDHD1 | WD repeat and HMG-box DNA binding protein 1 |
| 0 204752_x_at | NM_005484.2 | 10038 | PARP2 | poly (ADP-ribose) polymerase family, member 2 |
| 0 205034_at | NM_057749.1 | 9134 | CCNE2 | cyclin E2 |
| 0 205063_at | NM_001009182.1 | 8487 | SIP1 | survival of motor neuron protein interacting protein 1 |
| 0 205234_at | NM_004696.1 | 9122 | SLC16A4 | solute carrier family 16 (monocarboxylic acid transporters), member 4 |
| 0 205296_at |  | 5933 | RBL1 | Caution, check this probeset carefully. This probeset may detect an unusual splice variant, alternate termination site, or extended transcript of retinoblastoma-like 1 (p107) |
| 0 205395_s_at | NM_005590.3 | 4361 | MRE11A | MRE11 meiotic recombination 11 homolog A (*S. cerevisiae*) |
| 0 205436_s_at | NM_002105.2 | 3014 | H2AFX | H2A histone family, member X |
| 0 205733_at | NM_000057 | 641 | BLM | Bloom syndrome |
| 0 206074_s_at | NM_002131.2 | 3159 | HMGA1 | high mobility group AT-hook 1 |
| 0 206272_at | NM_006542.2 | 10638 | SPHAR | S-phase response (cyclin-related) |
| 0 206316_s_at | NM_014708.3 | 9735 | KNTC1 | kinetochore associated 1 |
| 0 206445_s_at | NM_198318.1 | 3276 | HRMT1L2 | HMT1 hnRNP methyltransferase-like 2 (*S. cerevisiae*) |
| 0 207183_at | NM_006143.1 | 2842 | GPR19 | G protein-coupled receptor 19 |
| 0 207268_x_at | X95632.1 | 10152 | ABI2 | abI interactor 2 |
| 0 207416_s_at | NM_004555.2 | 4775 | NFATC3 | nuclear factor of activated T-cells, cytoplasmic, calcineurin-dependent 3 |
| 0 207740_s_at | NM_012346.3 | 23636 | NUP62 | nucleoporin 62 kDa |
| 0 208149_x_at | NM_030655.2 | 1663 | DDX11 | DEAD/H (Asp-Glu-Ala-Asp/His) box polypeptide 11 (CHL1-like helicase homolog, *S. cerevisiae*) |
| 0 208159_x_at | NM_030655.2 | 1663 | DDX11 | DEAD/H (Asp-Glu-Ala-Asp/His) box polypeptide 11 (CHL1-like helicase homolog, *S. cerevisiae*) |
| 0 208741_at | NM_005870.3 | 10284 | SAP18 | sin3-associated polypeptide, 18 kDa |
| 0 208760_at | NM_003345 | 7329 | UBE2I | ubiquitin-conjugating enzyme E2I (UBC9 homolog, yeast) |
| 0 208765_s_at | NM_005826.2 | 10236 | HNRPR | heterogeneous nuclear ribonucleoprotein R |
| 0 208931_s_at | NM_004516.2 | 3609 | ILF3 | interleukin enhancer binding factor 3, 90 kDa |
| 0 209046_s_at | NM_007285.6 | 11345 | GABARAPL2 | GABA(A) receptor-associated protein-like 2 |
| 0 209052_s_at | NM_014919.1 | 7468 | WHSC1 | Wolf-Hirschhorn syndrome candidate 1 |
| 0 209068_at | NM_005463.2 | 9987 | HNRPDL | heterogeneous nuclear ribonucleoprotein D-like |
| 0 209172_s_at | NM_016343.3 | 1063 | CENPF | centromere protein F, 350/400ka (mitosin) |
| 0 209375_at | NM_004628.3 | 7508 | XPC | xeroderma pigmentosum, complementation group C |
| 0 209856_x_at | BT009920.1 | 10152 | ABI2 | abI interactor 2 |
| 0 210115_at | NM_052969.1 | 116832 | RPL39L | ribosomal protein L39-like |
| 0 210175_at | NM_003203 | 6936 | C2orf3 | chromosome 2 open reading frame 3 |
| 0 210334_x_at | NM_001168.2 | 332 | BIRC5 | baculoviral IAP repeat-containing 5 (survivin) |

TABLE 1-continued

Probeset data information

| Probe ID | GenBank ID | Entrez Gene ID | Gene Symbol | Gene description |
|---|---|---|---|---|
| 0 210527_x_at | NM_006001.1 | 7278 | TUBA2 | tubulin, alpha 2 |
| 0 210568_s_at | NM_002907.2 | 5965 | RECQL | RecQ protein-like (DNA helicase Q1-like) |
| 0 211814_s_at | NM_057735.1 | 9134 | CCNE2 | cyclin E2 |
| 0 211931_s_at | XM_370728.4 | 387933 | LOC387933 | heterogeneous nuclear ribonucleoprotein A3 pseudogene |
| 0 212202_s_at | NM_015497.2 | 25963 | TMEM87A | transmembrane protein 87A |
| 0 212219_at | NM_014614.1 | 23198 | PSME4 | proteasome (prosome, macropain) activator subunit 4 |
| 0 212297_at | XM_942079.1 | 79572 | ATP13A3 | ATPase type 13A3 |
| 0 212315_s_at | NM_024923.2 | 23225 | NUP210 | nucleoporin 210 kDa |
| 0 212316_at | NM_024923.2 | 23225 | NUP210 | nucleoporin 210 kDa |
| 0 212331_at | NM_005611.2 | 5934 | RBL2 | retinoblastoma-like 2 (p130) |
| 0 212343_at | AL117461.1 | 286451 | YIPF6 | Yip1 domain family, member 6 |
| 0 212621_at | NM_015257.1 | 23306 | KIAA0286 | KIAA0286 protein |
| 0 212832_s_at | NM_014756.2 | 9793 | CKAP5 | cytoskeleton associated protein 5 |
| 0 213215_at | AI910895 | 342236 | na | LOC342236 |
| 0 213253_at | AL833191.1 | 10592 | SMC2L1 | Caution, check this probeset carefully. It may detect an extended transcript of SMC2 structural maintenance of chromosomes 2-like 1 (yeast) |
| 0 213346_at | NM_138779.2 | 93081 | C13orf27 | chromosome 13 open reading frame 27 |
| 0 213453_x_at | NM_002046.3 | 2597 | GAPDH | glyceraldehyde-3-phosphate dehydrogenase |
| 0 213520_at | NM_004260 | 9401 | RECQL4 | RecQ protein-like 4 |
| 0 213947_s_at | NM_024923.2 | 23225 | NUP210 | nucleoporin 210 kDa |
| 0 214028_x_at | NM_030794 | 81550 | TDRD3 | tudor domain containing 3 |
| 0 214086_s_at | NM_005484.2 | 10038 | PARP2 | poly (ADP-ribose) polymerase family, member 2 |
| 0 214202_at | N21364 | | | |
| 0 214700_x_at | NM_018151.3 | 55183 | RIF1 | RAP1 interacting factor homolog (yeast) |
| 0 214727_at | NM_000059.2 | 675 | BRCA2 | breast cancer 2, early onset |
| 0 215006_at | AK023816 | | EZH2 | Caution, check this probeset carefully. This probeset may detect an alternate exon, alternate termination site, or overlapping transcript of enhancer of zeste homolog 2 |
| 0 215075_s_at | NM_002086.3 | 2885 | GRB2 | growth factor receptor-bound protein 2 |
| 0 215286_s_at | NM_020432.2 | 57157 | PHTF2 | putative homeodomain transcription factor 2 |
| 0 215509_s_at | NM_004336.2 | 699 | BUB1 | BUB1 budding uninhibited by benzimidazoles 1 homolog (yeast) |
| 0 215773_x_at | NM_005484.2 | 10038 | PARP2 | poly (ADP-ribose) polymerase family, member 2 |
| 0 216228_s_at | NM_001008396.1 | 11169 | WDHD1 | WD repeat and HMG-box DNA binding protein 1 |
| 0 217094_s_at | NM_031483.3 | 83737 | ITCH | itchy homolog E3 ubiquitin protein ligase (mouse) |
| 0 217640_x_at | NM_001039535.1 | 220134 | C18orf24 | chromosome 18 open reading frame 24 |
| 0 217805_at | NM_012218.2 | 3609 | ILF3 | interleukin enhancer binding factor 3, 90 kDa |
| 0 218142_s_at | NM_016302.2 | 51185 | CRBN | cereblon |
| 0 218204_s_at | NM_024513.1 | 79443 | FYCO1 | FYVE and coiled-coil domain containing 1 |
| 0 218381_s_at | NM_001012478.1 | 11338 | U2AF2 | U2 (RNU2) small nuclear RNA auxiliary factor 2 |
| 0 218432_at | NM_012175.3 | 26273 | FBXO3 | F-box protein 3 |
| 0 218602_s_at | NM_017645.3 | 54801 | FAM29A | family with sequence similarity 29, member A |
| 0 218869_at | NM_012213 | 23417 | MLYCD | malonyl-CoA decarboxylase |
| 0 218966_at | NM_018728.1 | 55930 | MYO5C | myosin VC |
| 0 219000_s_at | NM_024094.1 | 79075 | DCC1 | defective in sister chromatid cohesion homolog 1 |
| 0 219135_s_at | NM_022773.1 | 64788 | TMEM112 | transmembrane protein 112 |
| 0 219506_at | NM_024579.1 | 79630 | C1orf54 | chromosome 1 open reading frame 54 |
| 0 219556_at | NM_025108.2 | 80178 | C16orf59 | chromosome 16 open reading frame 59 |
| 0 219918_s_at | NM_018136.2 | 259266 | ASPM | asp (abnormal spindle)-like, microcephaly associated (*Drosophila*) |
| 0 219990_at | NM_024680.2 | 79733 | E2F8 | E2F transcription factor 8 |
| 0 220085_at | NM_018063 | 3070 | HELLS | helicase, lymphoid-specific |
| 0 220238_s_at | NM_001031710.1 | 55975 | KLHL7 | kelch-like 7 (*Drosophila*) |
| 0 220295_x_at | AK022792.1 | 55635 | DEPDC1 | DEP domain containing 1 |
| 0 220753_s_at | NM_015974.1 | 51084 | CRYL1 | crystallin, lambda 1 |
| 0 220788_s_at | AY256461.1 | 55072 | RNF31 | ring finger protein 31 |
| 0 220840_s_at | NM_018186.2 | 55732 | C1orf112 | chromosome 1 open reading frame 112 |
| 0 221012_s_at | NM_030912.1 | 81603 | TRIM8 | tripartite motif-containing 8 |
| 0 221156_x_at | BC027621.1 | 9236 | CCPG1 | cell cycle progression 1 |
| 0 221203_at | NM_018023.3 | 55689 | YEATS2 | YEATS domain containing 2 |
| 0 221476_s_at | NM_002948.2 | 6138 | RPL15 | ribosomal protein L15 |
| 0 221511_x_at | NM_004748.3 | 9236 | CCPG1 | cell cycle progression 1 |
| 0 221564_at | NM_001535 | 3275 | HRMT1L1 | HMT1 hnRNP methyltransferase-like 1 (*S. cerevisiae*) |
| 0 221703_at | NM_032043.1 | 83990 | BRIP1 | BRCA1 interacting protein C-terminal helicase 1 |
| 0 221825_at | NM_144567.3 | 90806 | ANGEL2 | angel homolog 2 (*Drosophila*) |
| 0 49452_at | NM_001093.2 | 32 | ACACB | acetyl-Coenzyme A carboxylase beta |
| 0 57703_at | NM_152699.2 | 205564 | SENP5 | SUMO1/sentrin specific peptidase 5 |

---

What is claimed is:

1. A method of predicting clinical tumor outcome in patients diagnosed with Stage I-III Lung Carcinoma comprising the steps of:
   establishing a plurality of gene expression values in a tumor sample wherein the plurality of gene expression values are a plurality of genes identified in Table 1;
   normalizing the plurality of gene expression values in the tumor sample to a reference expression;
   defining at least one threshold value for the plurality of gene expressions;
   establishing a vote of single-gene classifiers further comprising the steps of:
      determining individual classifiers, further comprising:
         comparing the gene expressions to the at least one threshold value;
         selecting genes with expression levels above the at least one threshold value;
         selecting genes with expression levels below the at least one threshold value;
         assigning a positive value to the selected genes with expression levels above the at least one threshold value and assigning a negative value to the selected genes with expression levels below the at least one threshold value to form probeset data;
      summing the probeset data to form a risk score; and
      comparing the risk score to a sum of the al number of genes tested to form the majority vote classifier;
      wherein the majority classifier is indicative of tumor outcome, such that the risk ratio above 0.15 is indicative of poor outcome and a risk ratio below 0.15 is indicative of good outcome;
   administering treatment based on the outcome,
      where patients with good prognosis are treated by resection and adjuvant chemotherapy, curative radiation therapy, or curative chemotherapy; and
      where patients with poor prognosis are treated with palliative treatment.

2. The method of claim 1, wherein the at least one threshold value consist of an upper threshold value and lower threshold value selected from the group consisting of the upper 33% of the gene expression values, the lower 33% of the gene expression values, the upper 15% of the gene expression values, the lower 15% of the gene expression values, the upper 50% of the gene expression values, and the lower 50% of gene expression values.

3. The method of claim 2, further comprising the steps of:
   assigning +1 to gene expression values above the upper threshold value;
   assigning −1 to gene expression values below the lower threshold value; and
   assigning 0 to gene expression values at or above the lower threshold value or at or below the upper threshold value.

4. The method of claim 2, further comprising the steps of:
   assigning +1 to gene expression values above the threshold value; and
   assigning −1 to gene expression values at and below the threshold value.

5. The method of claim 1, further comprising the step of identifying hazard ratios for the risk score, wherein a hazard ratio is calculated from the majority vote classifier and a score greater than 1 indicates poor clinical outcome.

6. The method of claim 1, further comprising generating a probeset list, comprising:
   providing a first probeset;
   testing the first probeset against gene expression data for a tumor cell, wherein the gene expression data is compared to two threshold values;
   utilizing probes identified as significantly related to gene expression n a second probeset test;
   testing a second probeset against gene expression data for a tumor cell, wherein the gene expression data is compared to two threshold values, and wherein the second probeset includes probes identified as significantly related to gene expression in the first probeset test;
   utilizing probes from the second probeset identified as significantly related to gene expression in a third probeset test; and
   testing a third probeset against gene expression data for a tumor cell, wherein the gene expression data is compared to two threshold values, and wherein the third probeset includes probes identified as significantly related to gene expression in the second probeset test.

7. The method of claim 1, further comprising:
   combining at least one clinical parameter to the gene expression values, wherein the at least one clinical parameter is selected from the group consisting of tumor staging, history of prior cancers, lymph node involvement, smoking history, age, gender, operation type, last follow-up date, patient's status, CXR scan, CT scans, pulmonary function tests, time and site of recurrence, adjuvant treatment information, and combinations thereof.

8. The method of claim 1, further comprising obtaining the gene expression values from protein, further comprising:
   collecting RNA from the tumor sample
   generating cDNA from collected protein by subjecting the tumor sample protein to SEQ ID 1; and
   subjecting the cDNA to nucleic acid analysis.

9. The method of claim 1, wherein the nucleic acid analysis is microarray, polymerase chain reaction, chromatin immunoprecipitation, gene array, quantitative-polymerase chain reaction, and reverse transciptase polymerase chain reaction.

* * * * *

SEQUENCE LISTING

<160> NUMBER OF SEQ ID NOS: 1

<210> SEQ ID NO 1
<211> LENGTH: 39
<212> TYPE: DNA
<213> ORGANISM: T7 bacteriophage

<400> SEQUENCE: 1
ggccagtgaa ttgtaatacg actcactata gggaggcgg          39